(12) United States Patent
Ackland

(10) Patent No.: US 10,744,373 B2
(45) Date of Patent: *Aug. 18, 2020

(54) AUTOMATED PRESCRIPTION OF ACTIVITY BASED ON PHYSICAL ACTIVITY DATA

(71) Applicant: Performance Lab Technologies Limited, Auckland (NZ)

(72) Inventor: Jonathan Edward Bell Ackland, Auckland (NZ)

(73) Assignee: Performance Lab Technologies Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,892

(22) Filed: Aug. 30, 2019

(65) Prior Publication Data

US 2019/0388733 A1 Dec. 26, 2019

Related U.S. Application Data

(63) Continuation of application No. 15/035,090, filed as application No. PCT/NZ2014/050010 on Nov. 10, 2014, now Pat. No. 10,589,150.

(30) Foreign Application Priority Data

Nov. 8, 2013 (NZ) .............................. 20130617514

(51) Int. Cl.
*A63B 24/00* (2006.01)
*A61B 5/024* (2006.01)
(Continued)

(52) U.S. Cl.
CPC .......... *A63B 24/0075* (2013.01); *A61B 5/021* (2013.01); *A61B 5/024* (2013.01);
(Continued)

(58) Field of Classification Search
None
See application file for complete search history.

(56) References Cited

U.S. PATENT DOCUMENTS 7,717,827 B2  5/2010  Kurunmaki et al.
7,771,320 B2 * 8/2010  Riley ................. A63B 24/0006
                                                          482/9
(Continued)

FOREIGN PATENT DOCUMENTS

EP    1159989    12/2001
NL    1027059    3/2006

OTHER PUBLICATIONS

Extended European Search Report for EP Application No. 14859524.2 dated Jun. 21, 2017, 8 pages.

*Primary Examiner* — Paul A D'Agostino
(74) *Attorney, Agent, or Firm* — Lowenstein Sandler LLP

(57) ABSTRACT

The technology disclosed here involves analyzing an activity session. An example method involves receiving activity data indicative of an activity of a user, the activity data comprising a plurality of measurements associated with multiple parameters monitored during an activity session; retrieving a set of criteria corresponding to an activity type, wherein the set comprises a criterion related to a biomedical parameter and a criterion related to a resistance parameter; classifying, based on the set of criteria, the received activity data into a plurality of segments, wherein a first segment comprises a portion of the activity data corresponding to the activity type; accessing historical data associated with the user, the historical data comprising a second segment of historical data corresponding to the activity type; comparing the first segment comprising the portion of the received activity data and the second segment comprising historical data; and generating output based on the comparing.

30 Claims, 9 Drawing Sheets

(51) Int. Cl.
*A61B 5/08* (2006.01)
*A61B 5/11* (2006.01)
*G06F 19/00* (2018.01)
*A61B 5/00* (2006.01)
*G06K 9/00* (2006.01)
*G16H 20/30* (2018.01)
*A61B 5/0205* (2006.01)
*A61B 5/021* (2006.01)
*A61B 5/0402* (2006.01)
*A61B 5/1455* (2006.01)

(52) U.S. Cl.
CPC ........ *A61B 5/0205* (2013.01); *A61B 5/02405* (2013.01); *A61B 5/0402* (2013.01); *A61B 5/08* (2013.01); *A61B 5/1112* (2013.01); *A61B 5/1114* (2013.01); *A61B 5/1118* (2013.01); *A61B 5/14552* (2013.01); *A61B 5/4836* (2013.01); *A61B 5/4866* (2013.01); *A63B 24/0062* (2013.01); *G06F 19/3481* (2013.01); *G06K 9/00342* (2013.01); *G16H 20/30* (2018.01); *A61B 2503/10* (2013.01); *A63B 2024/0068* (2013.01); *A63B 2220/17* (2013.01); *A63B 2220/18* (2013.01); *A63B 2220/22* (2013.01); *A63B 2220/72* (2013.01); *A63B 2220/73* (2013.01); *A63B 2220/75* (2013.01); *A63B 2220/76* (2013.01)

(56) References Cited

U.S. PATENT DOCUMENTS

| Patent/Pub No. | Date | Inventor | Classification |
|---|---|---|---|
| 8,033,959 B2 * | 10/2011 | Oleson | H04H 60/90 482/9 |
| 9,665,873 B2 * | 5/2017 | Ackland | A63B 24/0075 |
| 2001/0001303 A1 * | 5/2001 | Ohsuga | A63B 24/00 482/5 |
| 2007/0219059 A1 | 9/2007 | Schwartz et al. | |
| 2008/0204225 A1 * | 8/2008 | Kitchen | A63B 21/072 340/539.22 |
| 2008/0214360 A1 * | 9/2008 | Stirling | A61B 5/1038 482/9 |
| 2009/0233770 A1 | 9/2009 | Vincent et al. | |
| 2009/0262088 A1 * | 10/2009 | Moll-Carrillo | A63B 24/0062 345/173 |
| 2010/0048358 A1 * | 2/2010 | Tchao | G06F 19/3418 482/9 |
| 2010/0075806 A1 * | 3/2010 | Montgomery | A63B 24/0003 482/8 |
| 2011/0152696 A1 * | 6/2011 | Ryan | A61B 5/222 600/481 |
| 2013/0041590 A1 * | 2/2013 | Burich | G06F 19/3418 702/19 |
| 2013/0053990 A1 | 2/2013 | Ackland | |

* cited by examiner

AUTOMATED PRESCRIPTION OF ACTIVITY BASED ON PHYSICAL ACTIVITY DATA

RELATED APPLICATIONS

The present application is a continuation of application Ser. No. 15/035,090, filed May 6, 2016, entitled "Automated Prescription of Activity Based on Physical Activity Data" which is a National Phase entry of PCT/NZ2014/050010, filed Nov. 10, 2014, which claims the benefit of priority to New Zealand Patent Application No. 617514, filed Nov. 8, 2013, the contents of each being hereby incorporated by reference herein in their entireties

FIELD OF INVENTION

The invention relates to exercise and/or activity monitoring and in particular to interpretation of activity and exercise data for exercise plan or activity plan adjustment and for providing coaching feedback to a user.

BACKGROUND

Exercise and activity devices that measure biometric and environmental data such as heart rate, speed, leg or arm turnover or stroke rate, altitude, temperature, heart rate variability, power, slope, distance per turnover, location, distance, time and other parameters currently exist. This data is displayed on a watch or device screen or spoken through headphones. These systems are measuring or data devices.

These devices are unable to clearly interpret collected data and provide solutions to improve a user's physical abilities in fitness and sports training. FIG. 1 demonstrates the difficulty in interpreting currently available recorded raw data that is provided to users for their own analysis. This means that once the activity data is collected, the user must have the relevant level of skill to analyse and interpret it and then decide upon the changes that they would make to their future exercise to optimize their time and effort during training and to maximize the improvements. This currently occurs post exercise but also in real time but in all cases requires someone skilled in the art to analyse the data.

In most cases, users ultimately do not want data from a measuring device which is the current paradigm, they want to know what was correct about what they did, what problems and solutions they need to work on and what to do next. They need someone or something to interpret the data and provide intelligent feedback.

Hundreds of millions of people around the world exercise ineffectively due to poor understanding of the appropriate strategies to maximizing fitness, sports performance and health improvements through activity. In a percentage of cases incorrect activity and exercise methods lead to needless and avoidable injury, illness and even death which is both unfortunate and costly.

Most people engage in exercise and activity without the presence of someone skilled in the art to guide them.

Should they exercise for longer? Should they do another hill? Should they do speed work or should they stop?

This is extremely important and relevant currently for creating safer, more effective activity and exercise.

One issue is to find a way to utilise sensors and algorithms to provide prescriptive plan changes and coaching advice to an unsupervised user engaged in exercise and activities.

This problem requires a method for understanding what the user is doing through contextualising and classifying different user activity into Activity Type segments and an ability to update these activities into the future and potentially provide advice that causes the user to make modifications to future activities.

There have been a number of attempts to correct this problem.

De Vries 2001 application EP1159989 disclosed a method, device and system for generating and/or adjusting a training schedule based on data or preferences that are input by a user or automatically from one or more sensors. It also discloses a server system for selecting a training schedule from a database or adjusting an earlier schedule in accordance with obtained parameters.

It does not disclose contextualisation of an activity segment or a classification of an activity within a period of different activities. It also does not disclose automated modifications of future activity segments within a period of different activities or providing coaching advice based on modifications to future activity.

In 2004 van Diemen disclosed in NL1027059 a method, device and system for generating and/or adjusting a training schedule.

Contextualisation of an activity segment or classification of an activity were not disclosed. Automated modifications of future activity segments and providing advice based on future activity segment modifications was also not disclosed.

Kurunmaki in U.S. Pat. No. 7,717,827 disclosed a method and system for determining and adapting a training plan for a user based on a training load for a user within a template and progress within a template. This was achieved with respect to a training load such that, over a time period, the user reaches a cumulative load target.

U.S. Pat. No. 7,717,827 did not disclose contextualisation of an activity segment or the classification of an activity and did not cover automated modifications of future activity segments or providing coaching advice based on modifications to future activity.

There have also been some attempts to solve parts of this problem but each method does not employ contextualisation of activity segments or the methodology of converting performance measures based on contextualised activity into modifications to an Activity Plan or advice on alterations in future behaviour for activity.

An example is that the state of the art has developed such that some level of classification is possible known as Training Zones. There is a significant problem with this current activity measurement paradigm in which coaching information and activity plan updates are based on a single parameter.

To explain, Training Zones involve a single measured parameter like heart rate, speed, power or limb turnover and are used where the user must maintain a prescribed level like heart rate within a band or zone like 165 to 175 heart beats per minute. (see FIG. 2) This is measured over time or distance. The Heart Rate Training Zones in FIG. 2 do not make anaylsis of the data any easier.

There are systems currently available where Training Zones can be classified and data can be recorded if it conforms to the prescribed parameter threshold as a classified 'Training Zone' measuring 'Time in Zone'.

BUT multiple parameters are not recorded in concert to classify an Activity Type and they are not used for the purposes of automated interpretation and coaching prescription and modification of a plan.

Training Zones are given names to indicate what they might be like so titles like 'fat loss zone' or 'E2 zone', 'Maximal zone', 'Race Pace zone' are used. While these zones are excellent for training, like "go into the Easy zone" or "go into the Fast zone" they are not very good for data analysis. This is because there are a number of assumptions made when using Training Zones.

It is assumed that when you should go into the Easy Training Zone that you're not going to be climbing a steep hill. Going into a Speed Training Zone assumes you are on the flat and not running up that steep hill.

These scenarios are sufficient if there is no need for accurate automated analysis but as soon as there is a requirement to measure accurately what the user is doing, other parameters are necessary.

Questions arise like was the 'Speed Training Zone' training conducted on the flat because if it was not on the flat, it shouldn't be classed as Speed Training because comparing Speed Training on the flat with Speed Training up a hill will lead to large errors in automated coaching feedback.

Training Zones are mono parameter classifications and therefore do not contextualise activity and any advice provided or modifications to an Activity Plan are subject to large errors.

The state of the art also employs a number of performance measures like EPOC, Training Effectiveness, Acute Training Load, Chronic Training Load, Training Stress Score, Heart Rate Variability, VO2max and exercise economy but each does not have a method for modifying Activity Type segments in planned future Activity Sessions or does not provide advice that modifies future behaviour for activity based on automated analysis of current Activity Type segments.

The state of the art also features some measures around compliance but once again these do not feature measuring Activity Type segments.

In some cases, coaches and trainers manually use multiple zones in concert with each other to describe how a user should train but do not use multiple parameters in concert to define the classification of an Activity Type to automatically detect data that conforms to particular parameter zone combinations for automatic classification, interpretation and for providing coaching prescription.

It is an object of the present invention to provide a method and system for accurate automated activity interpretation and prescription which can be in the form of advice or modification of an activity session or long term Activity Plan in real time or post activity, or to at least provide the public with a useful choice.

Multi parameter contextualisation for classifying activities is used for updating future classified Activity Type segments within an Activity session or within a long term Activity Plan and to provide advice on a user's behavioural modifications to future activity.

SUMMARY OF THE INVENTION

In an embodiment the invention comprises a method of monitoring an activity session. The method comprises receiving activity data indicative of at least one activity performed during the activity session, the activity data comprising a plurality of measurements associated to a plurality of parameters monitored during the activity session; a processor comparing at least some of the received measurements associated to at least two of the parameters with at least one set of a plurality of sets of measurements stored on a tangible computer readable medium; and a processor generating a training plan based at least partly on a comparison between the received measurements and the stored measurements.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Preferably the plurality of sets of stored measurements are associated to respective activity types.

Preferably the method further comprises determining an activity type within the activity session at least partly from comparing the at least some of the received measurements with the sets of stored measurements.

Preferably one of the parameters comprises an effort parameter. Preferably the effort parameter comprises one of heart rate, speed, heart rate variability, respiration rate, power, energy expenditure, acceleration and force.

Preferably one of the parameters comprises a resistance parameter. Preferably the resistance parameter comprises one of altitude, slope, gradient, stride rate, stroke rate, cadence, and distance per limb turnover.

Preferably comparing the received measurements associated to the resistance parameter comprises determining an increase in altitude, a decrease in altitude and/or a constant altitude.

Preferably one of the parameters comprises a turnover parameter. Preferably the turnover parameter comprises one of stride rate, cadence, and stroke rate.

Preferably one of the parameters comprises a biomedical parameter. Preferably the biomedical parameter comprises one of ECG and BP.

Preferably one of the parameters comprises a biomechanical parameter. Preferably the biomechanical parameter comprises one of vertical oscillation, leg power balance, arm power balance, power through range of motion, footstrike impact, time on ground, and footstrike pattern.

Prerably one of the parameters comprises an enviromental parameter. Preferably the environmental parameter comprises one of temperature, humidity, and wind speed.

Preferably one of the parameters comprises a cardiorespiratory parameter. Preferably the cardiorespiratory parameter comprises one of oxygen updake and oxygen saturation.

Preferably comparing the received measurements associated to the at least two parameters includes comparing the received measurements against at least one lower threshold.

Preferably comparing the received measurements associated to the at least two parameters includes comparing the received measurements against at least one upper threshold.

Preferably comparing the received measurements associated to the effort parameter comprises comparing the received measurements against at least one lower threshold and at least one upper threshold.

Preferably the stored measurements comprise a training plan.

Preferably comparing the received measurements associated to at least two parameters includes determining conformity with the training plan.

Preferably conformity with the training plan is determined at least partly from one or more of duration, distance, intensity, number of distinct activity types, number of instances of an activity type, and rest periods between activity types.

Preferably comparing the received measurements associated to at least two parameters includes determining one of an improvement, static state, and deterioration in physical ability.

Preferably the method further comprises determining one or more physiological performance measures. Preferably the performance measure(s) include(s) one or more of cardiovascular, neurocardio, and muscular.

Preferably comparing the received measurements associated to at least two parameters includes determining an overall performance measure.

Preferably the method further comprises determining an overall performance measure at least partly from scores assigned to one or more of endurance, strength endurance, and speed.

Preferably the training plan represents a planned workout to be performed by a user.

Preferably the method further comprises transmitting an alert to a user while the user performs the planned workout.

Preferably the alert comprises an instruction to the user to modify the planned workout.

Preferably the alert comprises a modification to the training plan.

Preferably the training plan represents historical workout data associated to a user.

Preferably generating the training plan comprises generating a modification to an existing training plan.

Preferably the training plan represents a modification based on a benchmark parameter.

Preferably the method further comprises transmitting an alert to a user while the user performs the activity session.

Preferably the alert comprises an instruction to the user to modify the activity session.

In an embodiment the invention comprises a tangible computer readable medium having stored thereon computer-executable instructions that, when executed by a processor, cause the processor to perform at least one method described herein.

In an embodiment the invention comprises an activity monitoring system. The system comprises a display; a processor; and a tangible computer readable medium having stored thereon computer-executable instructions that, when executed by a processor, cause the processor to perform at least one method described herein.

In an embodiment the invention comprises an exercise coaching system. The system comprises a data acquisition module adapted to receive activity data indicative of at least one activity performed during an activity session, the activity data comprising a plurality of measurements associated to a plurality of parameters monitored during the activity session; a classification engine adapted to compare at least some of the received measurements associated to at least two of the parameters with at least one set of a plurality of sets of measurements stored on a tangible computer readable medium; and a training plan generator adapted to generate a training plan based at least partly on a comparison between the received measurements and the stored measurements.

Preferably the system further comprises a plurality of data measurement devices adapted to measure activity data indicative of at least one activity performed during the activity session, the data acquisition module adapted to receive the activity data from the data measurement devices.

Preferably the system further comprises an alert generator configured to generate an alert.

Preferably the plurality of sets of stored measurements are associated to respective activity types.

Preferably the classification engine is adapted to determine an activity type within the activity session at least partly from comparing the at least some of the received measurements with the sets of stored measurements.

Preferably one of the parameters comprises an effort parameter. Preferably the effort parameter comprises one of heart rate, speed, heart rate variability, respiration rate, power, energy expenditure, acceleration and force.

Preferably one of the parameters comprises a resistance parameter. Preferably the resistance parameter comprises one of altitude, slope, gradient, stride rate, stroke rate, cadence, and distance per limb turnover.

Preferably the classification engine is adapted to determine an increase in altitude, a decrease in altitude and/or a constant altitude.

Preferably one of the parameters comprises a turnover parameter. Preferably the turnover parameter comprises one of stride rate, cadence, and stroke rate.

Preferably one of the parameters comprises a biomedical parameter. Preferably the biomedical parameter comprises one of ECG and BP.

Preferably one of the parameters comprises a biomechanical parameter. Preferably the biomechanical parameter comprises one of vertical oscillation, leg power balance, arm power balance, power through range of motion, footstrike impact, time on ground, and footstrike pattern.

Preferably one of the parameters comprises an enviromental parameter. Preferably the environmental parameter comprises one of temperature, humidity, and wind speed.

Preferably one of the parameters comprises a cardiorespiratory parameter. Preferably the cardiorespiratory parameter comprises one of oxygen updake and oxygen saturation.

Preferably the classification engine is adapted to compare the received measurements against at least one lower threshold.

Preferably the classification engine is adapted to compare the received measurements against at least one upper threshold.

Preferably the classification engine is adapted to compare the received measurements against at least one lower threshold and at least one upper threshold.

Preferably the stored measurements comprise a training plan.

Preferably the system further comprises a compliance engine adapted to determine conformity of the received measurements associated to at least two parameters with the training plan.

Preferably the compliance engine determines conformity with the training plan at least partly from one or more of duration, distance, intensity, number of distinct activity types, number of instances of an activity type, and rest periods between activity types.

Preferably the system further comprises a performance engine adapted to determine one of an improvement, static state, and deterioration in physical ability.

Preferably the performance engine is adapted to determine one or more physiological performance measures.

Preferably the performance measure(s) include(s) one or more of cardiovascular, neurocardio, and muscular.

Preferably the performance engine is adapted to determine an overall performance measure.

Preferably the performance engine is adapted to determine an overall performance measure at least partly from scores assigned to one or more of endurance, strength endurance, and speed.

Preferably the training plan represents a planned workout to be performed by a user.

Preferably the training plan represents historical workout data associated to a user.

Preferably the training plan generator is adapted to generate a modification to an existing training plan.

Preferably the training plan represents a modification based on a benchmark parameter.

Preferably the alert generator is adapted to transmit an alert to a user while the user performs a planned workout.

Preferably the alert comprises an instruction to the user to modify a planned workout.

Preferably the alert comprises a modification to a training plan.

Preferably the alert generator is adapted to generate an alert to a user while the user performs an activity session.

Preferably the alert comprises an instruction to the user to modify the activity session.

Described herein is a method of analysing an activity session comprising:

receiving activity data over a period of time or distance indicative of one or more activities performed during the activity session, said data relating to at least one parameter monitored during the activity session, and utilising an exercise coaching system to compare current data for an Activity Type segment within a workout with historic data for like Activity Type segment data and benchmark data thresholds where improvements and deteriorations found in comparisons elicit automated modifications of aspects of future Activity Type segments, the coaching system defining a modification based on at least one satisfied threshold criteria from at least one monitored parameter.

and/or utilising an exercise coaching system to compare current data for an Activity Type segment within a workout with historic data for like Activity Type segment data and benchmark data thresholds where improvements and deteriorations found in comparisons elicit automated coaching advice, regarding user modifications of aspects of future activity, the coaching system defining a modification based on at least one satisfied threshold criteria from at least one monitored parameter.

Preferably the at least one parameter monitored during the activity session is obtained from an activity monitoring device and the activity data is received from the monitoring device. Preferably the data is received in real time. Alternatively the data is received post activity. Preferably the device is wearable.

Preferably the data is received as a data stream for each of the monitored parameter(s) or as an Activity Type segment, and utilising a classification system comprises:

trawling through at least one data stream and comparing data points in the stream against one or more pre-stored threshold criteria associated with the parameter relating to that stream, determining when corresponding data points of the data streams relating to the parameters associated with a particular activity satisfy the one or more threshold criteria defining the activity, and associating the activity with the data points.

The data may be received and trawled automatically or alternatively the system is arranged to enable a user to manually time, distance or location stamp a block of activity data (e.g. by pushing a time, distance or location stamp or lap split button on a device) and the stamped block for each monitored parameter is trawled and compared against one or more threshold criteria.

Preferably the method further comprises:

processing the data points associated with each activity to determine a level of cardiovascular or muscular performance for the activity. Preferably processing comprises applying one or more algorithms that include defining the physiology of Endurance, Strength Endurance or Speed to the classified data points to determine the level of performance.

Preferably the method further comprises:

composing a response based on the level of performance or the classified data points or both, and outputting the response to the user.

The response may be output in an auditory, graphical and/or text form and may be output to the user in real time or post activity.

The response for example may be in the form of coaching advice which may alter how the user engages in a particular activity thereby optimising their exercise or activity. It may also alter an activity plan associated with the user.

Coaching advice is information supplied regarding optimising a type of activity either by better compliance or technique or based on performance measures and must involve a detection and a solution component, The response may also be manually or automatically output.

Preferably the method further comprises prior to receiving the activity data presenting or downloading onto a device a fully dynamic and configurable activity plan comprising one or more Activity Types to be performed over multiple activity sessions into the future.

Preferably the activity or workout plan is composed of an overall activity or workout duration and Activity Type segments within the workout.

Activity Type segments are defined by multiple parameters used simultaneously to describe an activity being composed of an effort parameter like heart rate, power, respiration rate, force, acceleration and a resistance parameter like gradient or change in gradient, slope or change in slope, change in altitude, the gear a cyclist is in or distance per turnover. (e.g. stride length, distance per stroke, distance covered for a full pedal revolution).

Once Activity Type segments are defined in some cases they can be further described in terms of the duration of the Activity Type, number of instances that the Activity Type will occur within the overall activity or workout session, and durations of recovery periods between Activity Types.

Activities and Workouts are to some extent linked over time through a long term Activity Plan. This is because workout volumes (duration, distance or number of instances within a session) follow ascending and descending sequential progressions over time.

Instances of a particular Activity Type segment occurring over a long term Activity Plan are also linked in ascending and descending sequential progressions of volume (duration, distance or number of instances within a session).

Different Activity Types ascend and descend at different times through an Activity Plan in accordance with an overall organizational progression of all Activity Types. A long term Activity Plan will occur over one or more weeks.

Preferably the method further comprises updating the Activity Plan for a future activity session based on the response. (see FIG. 4 to see the feedback engine)

Updating the Activity Plan may involve overall workout or activity durations which may include a single workout or may update all sessions into the future of the Activity Plan.

Updating Activity Types within the workout or activity duration involve the number of Activity Type instances, the duration of the Activity Type, the rest periods between Activity Type which can include, effort intensities, turnover rates (e.g. stride rate), distance per turnover (e.g. stride length), force, work, accelerations, and slopes, gradients and terrain.

This may involve multiple Activity Types within a workout or activity session.

Preferably the classification system utilises both multi-parameter zones to identify an activity.

Preferably the alterations to the activity plan involve alterations to multi parameter Activity Types. Activity Types are made up of parameters that describe them.

Preferably the adjusting of an Activity Type involves modifications to the length of the Activity Type, the number of times the Activity Type is performed during an activity session, the effort of the Activity Type and the terrain the Activity Type is performed on.

The measure of the length of the Activity Type includes a measure of duration or distance that the Activity Type should occur over or a combination of both parameters.

The measure of the number of times that the Activity Type should be performed in a workout involves the number of repetitions the Activity Type should be performed.

The measure of terrain that the Activity Type should be performed on includes altitude or change in altitude, slope or change in slope or gradient or change in gradient or any combination thereof.

The measure of effort involves a measure of heart rate or change in heart rate, speed or change in speed, power or change in power and respiration rate and change in respiration rate or any combination thereof. Heart rate, speed, power and respiration rate measures also include derivations of heart, speed, power and respiration rate including heart rate variability, EPOC, acceleration, force and other derivations.

Preferably coaching advice is defined by automatically generated commentary based on biomechanical technique, control of effort, Activity Plan and workout compliance, and performance measures.

Coaching advice based on biomechanical aspects may include limb turnover rate, distance per turnover, posture, variation in footfall time, degree of foot lift in running, variations between power delivery from left to right limb, ability to provide even power through a cyclic limb action, and pressure points on the foot or applied during the exercise action.

Coaching advice based on control of effort may include pacing, too much or too little effort in a workout, on the flat or on a hill.

Coaching advice based on Activity Plan and workout compliance may include commentary around the aspects of a workout schedule, future workouts, Activity Types and repetitions left to complete in a workout, and level of compliance to a workout or Activity Plan.

Coaching advice based around performance includes commentary on muscular performance levels, cardiovascular performance levels, speed, power, heart rate, and changes to the workout or Activity Plan based on performance measures which include derivations of these parameters.

The system applies to sports or activities that involve alternate (e.g. running, walking) and/or cyclic movement of limbs back and forth (e.g. cycling, swimming and kayaking) or where there is combined forwards and backwards movements of limbs. (e.g. rowing)

Described herein is an exercise coaching system for analysing and interpreting an activity session for the purposes of coaching prescription, the system comprising:

an interface for receiving Activity Type segment data indicative of one or more activities performed during the activity session, said data relating to at least one parameter monitored during the exercise session, a processing means for classifying data and comparing current data for an Activity Type segment within a workout with historic data for like Activity Type segment data thresholds and benchmark data thresholds where improvements and deteriorations found in comparisons elicit automated modifications of aspects of future Activity Type segments, the coaching system defining a modification based on at least one satisfied threshold criteria from at least one monitored parameter, a means of adjusting a workout plan or long term Activity Plan and providing forms of coaching advice to a user using the device, and/or a processing means for classifying data and comparing current data for an Activity Type segment within a workout with historic data for like Activity Type segment data thresholds and benchmark data thresholds where improvements and deteriorations found in comparisons elicit automated coaching advice regarding future Activity Type segments, the coaching system defining a modification based on at least one satisfied threshold criteria from at least one monitored parameter, a means of adjusting a workout plan or long term Activity Plan and providing forms of coaching advice to a user using the device, at least one memory component having a classification system, interpretative algorithms and rules for workout and long term Activity Plan adjustment, one or more workout plans and long term Activity Plans and coaching feedback stored therein, to generate modifications to a workout plan or long term Activity Plan and provide detection of training parameters and coaching advice to a user using the device.

Preferably the system further comprises one or more activity monitoring devices, each arranged to obtain data indicative of parameters monitored during an activity session.

Preferably the prescription module is remote from the one or more monitoring devices and each monitoring device is arranged to transmit the data indicative of the monitored parameters to the prescription module.

Preferably the system further comprises:

A central station for accommodating the prescription module, and

A receiver for receiving data indicative of multiple parameters monitored during an activity session from the one or more monitoring devices.

Alternatively the prescription module is housed within each monitoring device.

Preferably the alterations to the activity plan involve alterations to multi parameter Activity Types. Activity Types are made up of parameters that describe them.

Preferably the adjusting of an Activity Type involves modifications to the length of the Activity Type, the number of times the Activity Type is performed during an activity session, the effort of the Activity Type and the terrain the Activity Type is performed on.

The measure of the length of the Activity Type includes a measure of duration or distance that the Activity Type should occur over or in combination.

The measure of the number of times that the Activity Type should be performed in a workout involves the number of repetitions the Activity Type should be performed.

The measure of terrain that the Activity Type should be performed on includes altitude or change in altitude, slope or change in slope or gradient or change in gradient or any combination thereof.

The measure of effort involves a measure of heart rate or change in heart rate, speed or change in speed, power or change in power and respiration rate and change in respiration rate, Heart Rate Variability or a change in Heart Rate Variability or any combination thereof. Heart rate, speed, power and respiration rate measures also include derivations of heart, speed, power and respiration rate.

Preferably coaching advice is defined by automatically generated commentary based on biomechanical technique, control of effort, Activity Plan and workout compliance, and performance measures.

Coaching advice based on biomechanical aspects may include limb turnover rate, distance per turnover, posture, variation in footfall time, degree of foot left in running, variations between power delivery from left to right limb, ability to provide even power through a cyclic limb action, and pressure points on the foot or applied during the exercise action.

Coaching advice based on control of effort may include pacing, too much or too little effort in a workout, on the flat or on a hill.

Coaching advice based on Activity Plan and workout compliance may include commentary around the aspects of a workout schedule, future workouts, Activity Types and repetitions left to complete in a workout, and level of compliance to a workout or Activity Plan.

Coaching advice based around performance includes commentary on muscular performance levels, muscular performance levels, speed, power, heart rate, and changes to the workout or Activity Plan based on performance measures.

In this specification activity can mean any type of action performed by an individual or group of individuals over a period of time or distance (or both) which may or may not involve movement in general activity, such as lying, sitting down and walking and also sports activities such as running or cycling. An activity session or workout means a period of time or distance where an individual performs one or more activities. (Activity Types) Exercise and exercise sessions (or workout) are intended to be covered by the terms activity and activity sessions respectively. Activity period refers to the period within an activity session in which an activity is performed.

Activity Type means a method of describing a form of exercise where multiple parameters such as effort (e.g. heart rate, respiration rate or power) and resistance (e.g. terrain or distance per turnover) are used. Activity Types have thresholds or zones where when all the parameters conform the Activity Type is identified and when not all parameters match the system terminates the recording of the data under the label for the Activity Type and logs the data for analysis.

Multi Parameter does not mean parameters of the same data measured on different axes like a triaxial accelerometer where the same parameter; acceleration is measured on 3 axes at different orientations.

The term speed is a horizontal speed which can be measured by many sensors and can be inferred by an accelerometer if the correct algorithms are applied but does not mean that other motion measures using an accelerometer mean speed.

Prescription is a term that encompasses two forms of coaching guidance. In its first form, prescription is coaching advice that is elicited automatically when interpretative algorithms applied to the classified data and other non-classified data cause a coaching comment to be provided as feedback. The second form is prescription where a workout is changed in real time or future workouts are automatically modified in a long term Activity Plan based on applying interpretative algorithms to classified and non-classified data.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION

1. Virtual Coach System Overview

One aspect of the proposed method goes beyond the functionality of a data measurement device or a 'talking heart rate monitor'. The techniques described below classify, interpret and provide dynamic feedback to all those millions of users that have no coach or way of determining how to maximize their exercise and activity whether it be for sport, health or weight loss in real time or post activity.

Figure 5:
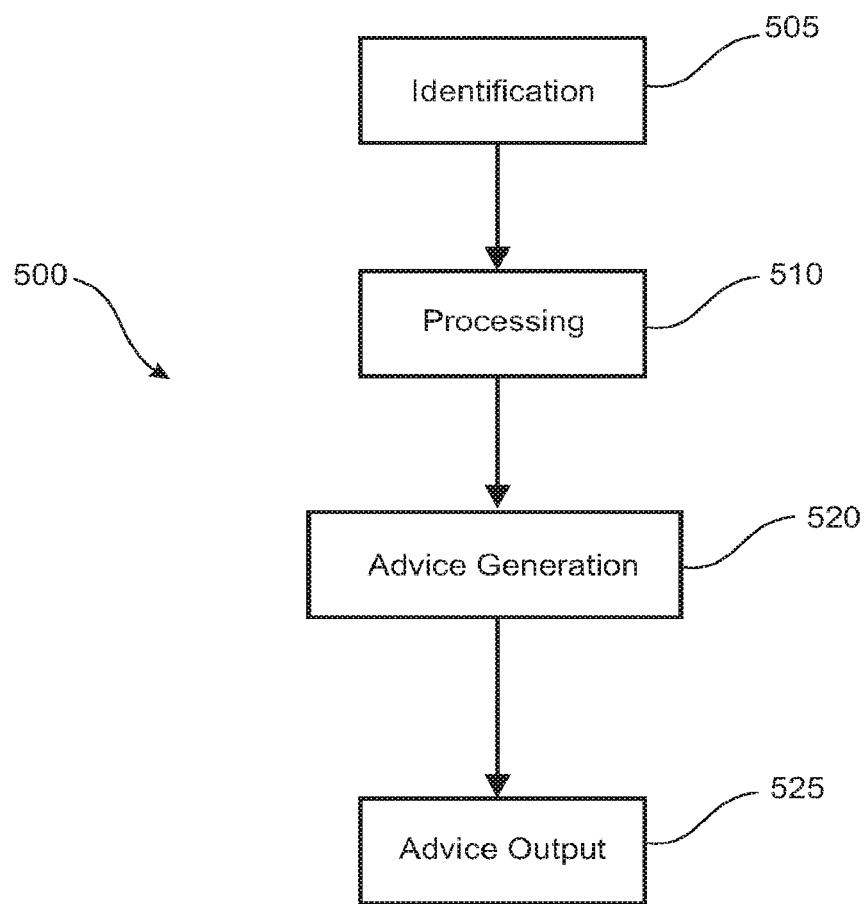
FIG. 5 is a flow diagram showing an overview of a preferred method of exercise analysis of the invention.

Referring to FIG. 5, an overview of a preferred method or a system flow diagram 500 for analysing an activity session is shown. A user of the system engaging in an activity session, either prior to or whilst the system is being used, gathers information or data related to the activity or activities performed during the session, preferably using at least one activity monitoring device and supplies it to the system to gain feedback and/or guidance in relation to their fitness goals. The information is received by the system either manually via the user initiating uploading of the information from one or more data measurement devices or automatically via one or more data measurement devices, or from some other source for analysis, and is received and/or analysed either during activity or post activity. The system may be part of the data measurement device or may be separate, running on a personal computer for example, or on a remote server accessible by and in communication with a personal computer and/or one or more monitoring devices. In each case, a Data Acquisition Module is employed to receive the data from such devices.

During analysis the system will identify at step 505 the different types of activities the user has engaged in (or is engaging in) during the activity session using a Classification Engine. A classification system, which will be described in more detail below, is used by the system to identify the activities performed by the user from the activity information/data received. The Classification Engine enables the overall system to partition the data into one or more data streams or blocks relating to the one or more activities performed by the user during the activity session. The data can then be processed and data is interpreted at step 510 while taking the type of activity performed into consideration. The classification system defines an activity based on at least one satisfied threshold criteria from at least one monitored parameter (other than distance or time or both which define the length of the activity or activity session but not the type of activity). In most embodiments, the Classification Engine defines an activity using multi-parameter zones (i.e. one or more threshold criteria from more than one parameter) that may occur within an activity session. This for example may be that during running any speed over 7 km/hr where the user has a change in altitude is defined as a 'hill climbing during running' activity, or any period that involves the user moving at 12-14 km/hr, while an accelerometer detects at least 160 steps per min over the period and while altitude does not change (flat), is defined as a 'running speed work' activity.

In accordance with the invention classified activities are identified using one or more data streams first (each stream being associated with one of the parameter(s) used to define a particular classified activity for example), then the data for the activity is processed specific to the defined activity as opposed to differently classified or non-classified activities that have slightly different definitions. The effect each type of activity has on the user's overall fitness, performance or fatigue is different and therefore it is necessary to distinguish between them to provide satisfactory analysis and appropriate advice. In some embodiments the data once classified is processed (510) for the various identified Activity Types to translate collective activity data into a tutorial or advice (step 520) for example. Proceessing of data requires a Performance Engine and a Compliance Engine to apply their diagnostics to the data received and identified by the Classification Engine. The data may be processed with or without the rest of the activity session data. The data relating to a particular activity may be processed against a plan, historic data, an ideal zone (the zone all users would ideally fall under—not specific to the history of the individual but rather applies to all individuals, e.g. an ideal zone for example is a pedal cadence of between 85 and 95 revolutions per minute for all cyclists riding at an easy pace), a threshold or environmental conditions for example. At 520 prescriptive modifications are made based on interpretative analysis produced by the Compliance and Performance Engines. These prescriptive modifications can use the Training Plan Generator or the Alert Generator Engines. In some embodiments a response is generated from the output of the processing stage which may be advice provided in the form of a prescription (method for modifying a plan) or a solution (method for modifying how a user engages in an activity) for example. The advice may be output (step 525) in either a text, auditory or graphical form as opposed to a visual or auditory display of raw or derived exercise data in real time or post activity.

Advice is a preferable feature of the invention and may alternatively not be supplied by the system but from a trainer or some other source for example. (See FIG. 4 to see how the Coaching Prescription Feedback Engines of FIG. 5 fits into the whole system.)

Figure 4:
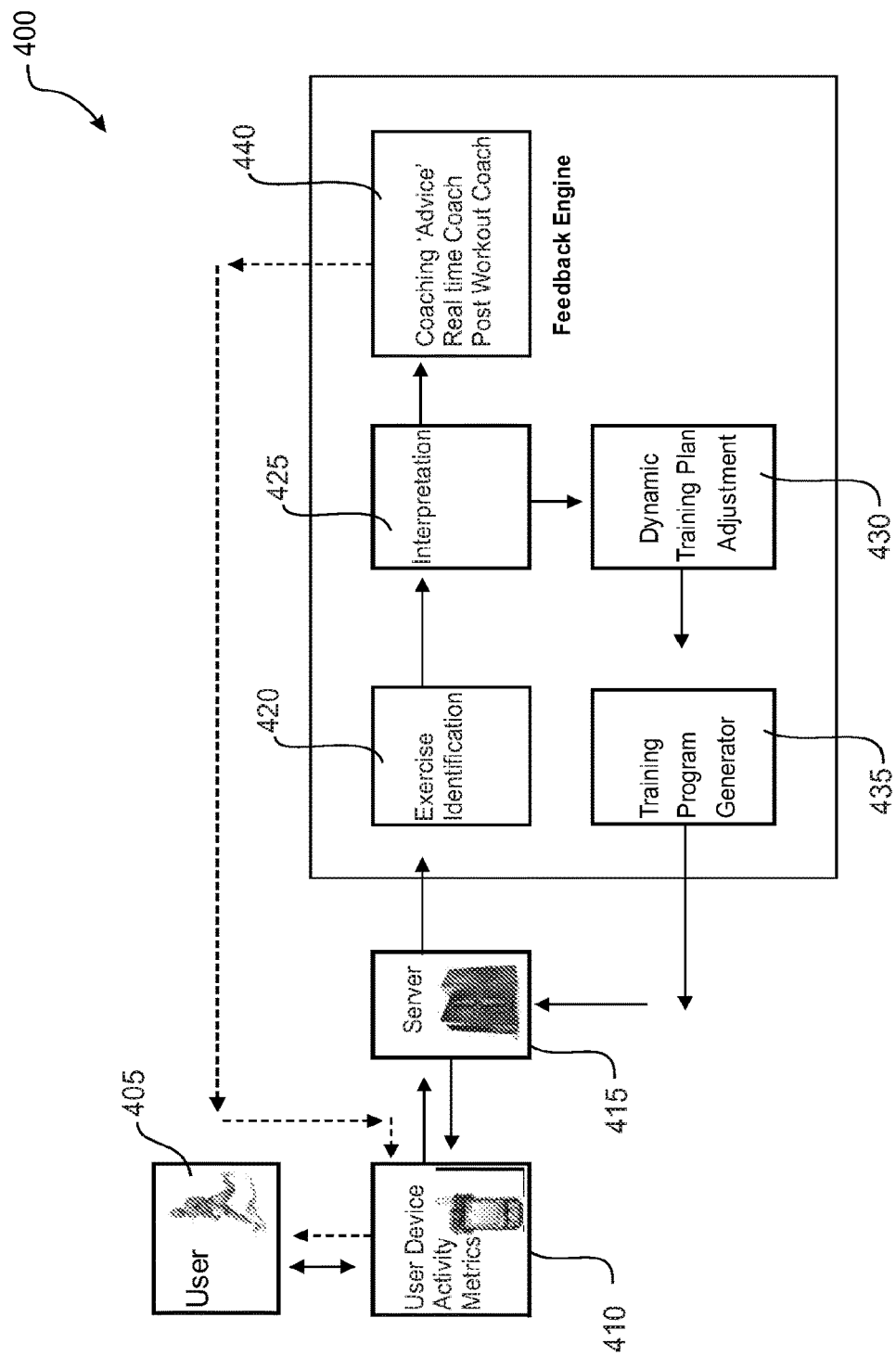
FIG. 4 is a table showing the elements of the exercise analysis and 'prescription (plan/workout adjustment and coaching advice) provided by the system known as the Feedback Engine.

In FIG. 4 at 405, a user is engaging in Activity which could include exercise. The user has a data measurement device which contains various sensors in 410. Data is taken in by Data Acquisition Module at 415 to be applied to the Coaching Prescription Feedback Engines. The Coaching Prescription Feedback Engines is a complete system made up of multiple engines. These include a Classification Engine, a Compliance Engine, a Performance Engine, a Training Plan Generator and an Alert Generator.

Data is first put through the Classification Engine at 420 to identify user activity. At 425, the Compliance Engine and Performance Engine process the data via automated analysis and interpretation of the classified data.

At 430, 435 and 440, advice generation is created either by providing an alert to the user through the Alert Generator (440) or by modifying their activity session or activity plan via the Training Plan Generator. (430 and 435)

In some embodiments, all the processes in FIG. 4 can occur on the users data measurement device.

In one embodiment the data is automatically received by the classification system in one or more streams and then trawled, with the data points being compared against one or more threshold criteria associated with the parameter relating to that stream. In an alternative embodiment the system may be arranged to enable a user to manually time, distance or location stamp a block of activity data (e.g. by pushing a time stamp or lap split button on a device) and the stamped block for each monitored parameter is then trawled and compared against the one or more threshold criteria. For both embodiments corresponding data points of the one or more streams or blocks (that relate to one or more parameters associated with a particular activity) are associated with a particular activity when the system recognizes that the data points satisfy the one or more threshold criteria defining that activity, and therefore associates the corresponding data points with the activity.

The raw data that defines Activity Types is preferably obtained from special purpose activity and exercise measurement devices.

2. The Anatomy of an Activity Plan

Coaching advice can occur in relation to a Training/Activity Plan or can provide more limited feedback without the user having a plan.

The following definitions provide context on how an Activity Plan works:

2.1 Activity Plan

An Activity Plan is a calendar of workouts or activity sessions over a series of days for an extended period of time, usually for a number of months. The plan is designed to generate the largest improvements specific to a chosen goal for the least time, effort and impact on the body. This is achieved by manipulating workouts and Activity Types in terms of volume and timing over an extended period of time allowing the body to gradually adapt to the various physical stimuli placed on it.

2.2 Workout or Activity Session

A workout is an activity session on a particular day which contains a set of different types of activities called Activity Types. The workout is usually for a set duration or distance.

2.3 Activity Type

Activity Types occur within a workout, which are training tasks to be performed within the workout/session. Workouts contain Activity Types of set durations, efforts and the number of times the activity should be repeated within a workout which are also known as repetitions. (reps)

A workout may be 60 mins in duration and contain the Activity Type; Hills and Up Tempo. The repetitions might be 4 hills and 2×2 mins at Up Tempo. This means that within the 60 min workout or activity the user has a prescription to complete 4 hills and do 4 mins of Up Tempo broken into 2 parts. Using the Activity Classification method which detects Activity Types, the user can choose when it is most appropriate to complete an Activity Type within the session.

2.4 Activity Plan, Workout, and Activity Type Combination

An Activity Plan is made up of a series of workouts that contain Activity Types, set within a calendar over a series of months that describe the activity tasks required to achieve a goal whether this be to compete in a sporting event, lose weight or maintain health.

The interpretation can be compliance, technique or performance based.

Compliance measures are used to determine how closely a user follows their Activity Plan. If the actual data closely matches the plan, compliance is high; if data does not closely match the plan, compliance is low. Compliance is made up of the number of hills completed and cumulative vertical meters ascended for Rolling Hills and Hills Activity Types. Duration and reps completed are the elements that make up compliance for Up Tempo and Anaerobic Threshold Activity Types. There is no compliance measure for the Easy Activity Type. Compliance can only be measured against an Activity Plan or prescribed workout/activity session.

Technique measures can include measurements of how the user conducts themselves within the workout. Stride rates, heaviness of foot strike and many other components can be used to provide feedback on technique. Technique measures can occur whether the user is following a plan or not.

Performance measures are also possible where fatigue and improvement can be ascertained. Elevated heart rates for a particular speed indicate fatigue for example and there are many other methods available within the prior art (e.g. HRV, R-R, VO2max, EPOC, Training Effect, Heart Rate Decoupling, ATL, CTL, TSS) that can be used. Performance measures can occur whether or not the user follows an Activity Plan.

3. System Processes

3.1 the Difference Between Activity Types and Training Zones

A workout or any activity is made up of different tasks or forms of exercise that can be characterized by a series of multiple simultaneous measured parameters breaking them up into Activity Type segments.

Activity Types form a continuous series of time or distance segments of multi-parameter data through all the raw data for the duration of the workout or activity session.

The cornerstone of this system is the use of Activity Types to classify data as opposed to the prior art method of using Training Zone classifications.

Activity Types are made up of multiple Training Zones and other parameters.

Figure 1:
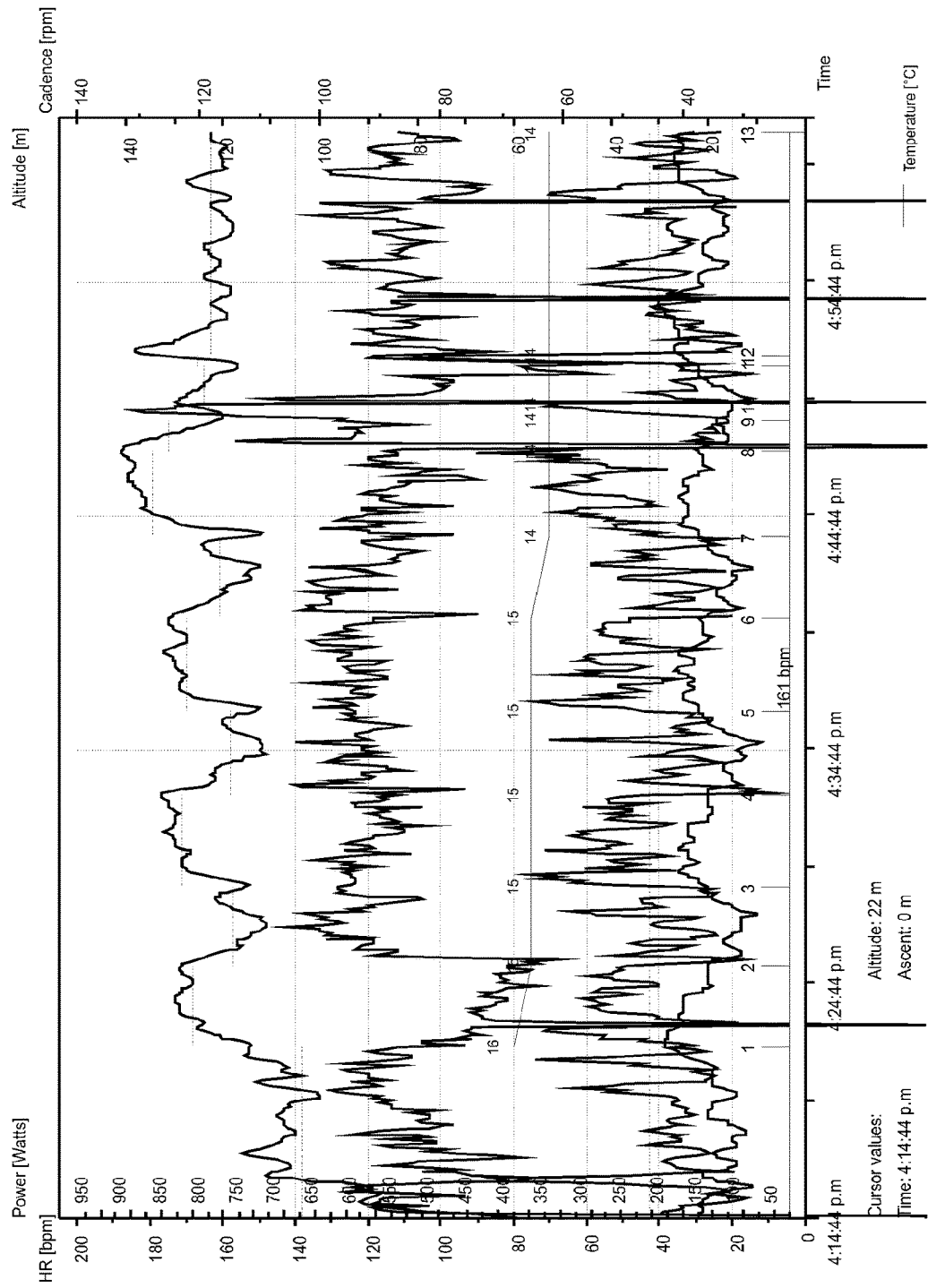
FIG. 1 shows a prior art data output from a biometric monitoring device, in this case a cycling monitor and presents what a non-expert user must interpret to adequately optimize their next exercise session.
Figure 2:
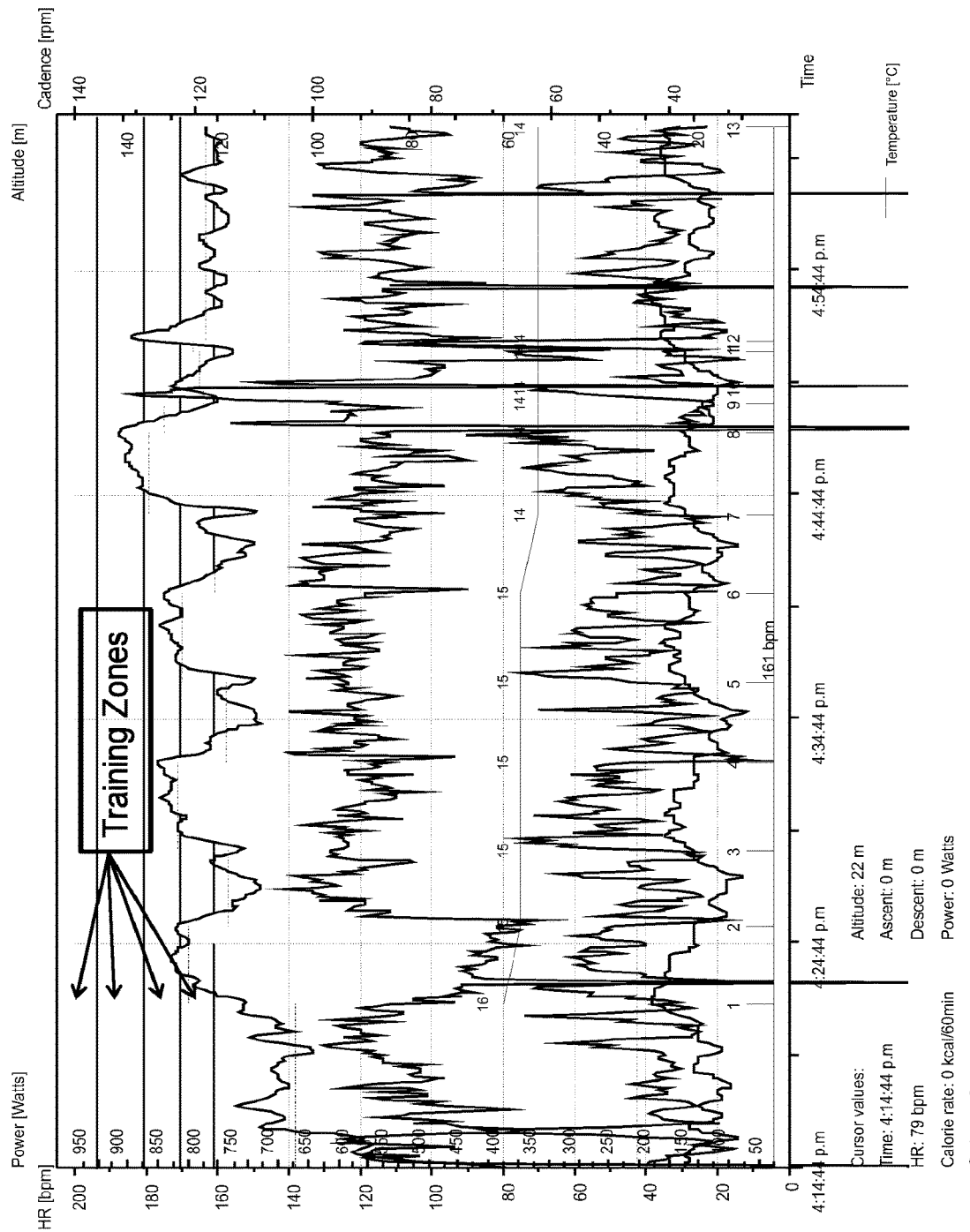
FIG. 2 shows typical prior art data output from a cycling biometric monitoring device utilizing heart rate Training Zones that are presented to the non-expert user for interpretation to optimize their next exercise session.
Figure 3:
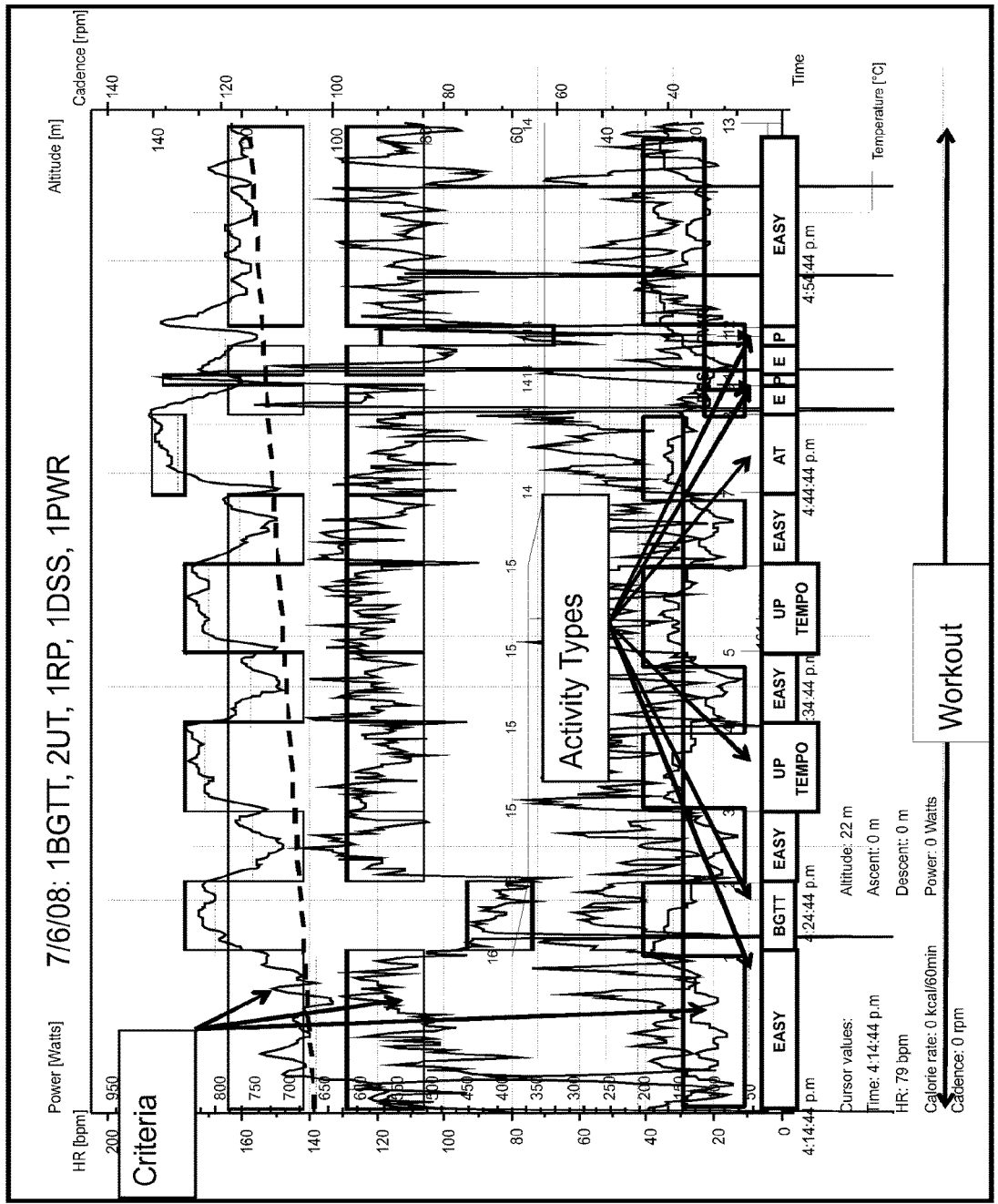
FIG. 3 shows example data from a cycling biometric monitoring device utilizing the classification system of the invention into Activity Type.

This means that any activity or exercise becomes a series of 'classified Activity Type segments' over the workout duration. FIG. 3 shows classification of cycling data where heart rate, cadence and altitude are measured over the duration of a workout and use of multiple parameter zones are used as criteria to classify activity into Activity Types within a Workout or Activity Session. These parameters are used to define classifications of different Activity Type segments which appear at the bottom of the graphic. A workout is therefore made up of a series of Activity Type segments which together form the complete workout.

Multi Parameter classification is critical to interpretation and coaching advice as it allows processing and interpreting data within an Activity Type segment or between Activity Type segments that contains the same label. This means that 'like' data is compared to 'like' data. It also breaks down all the possible ways the user can train into its component parts or 'building blocks' for analysis.

Because there are many environmental and physiological variables in activity and exercise, assumptions cannot be made for automated measurement. When a system automatically classifies activity or exercise, there is no coach or trainer to see what the user is doing so the usual assumptions that occur in manually managed training and for example, exercise where terrain is taken for granted; cannot occur. Terrain must be measured and brought in as part of a classification system to get accurate measurement of data for interpretation.

This is why classification of Activity Types must include at least one exercise parameter like heart rate for instance AND altitude change depicting terrain (uphill, flat, downhill) over a period of time or distance to accurately capture data correctly for analysis.

In an example demonstrating the problem with 'Training Zones', a runner may be running briefly at too high a heart rate which could be interpreted as training too hard but without other parameters this could be incorrect. If we look at speed measured in conjunction with the high heart rate values we find that the runner was actually running too slowly. If we also look at altitude change we see that they were actually running up a hill. The reason heart rate went up and speed went down is due to running up a hill. Using a single parameter Heart Rate Training Zone for measurement can lead to wholly inaccurate interpretations of what the user is doing.

Real life training and activity is slightly more complex than a mono-dimensional Training Zone. Real life training usually involves at least two key parameters for acyclic activities like walking, running, cycling and rowing. These are the effort level (depicted by heart rate, power or speed) and turnover usually depicted by stride rate, stroke rate or cadence. Different manipulations of these 2 factors can be used in cycling for example to match 'race pace' with a moderate load gear at a high cadence generating high cardiovascular effort, 'easy training' which is low muscular effort or a small gear at a moderate cadence, and forms of 'strength' loaded exercise in cycling like a big gear (high muscular effort) at a low cadence.

Each of these is also carried out on a terrain that may be flat, uphill or downhill and the combinations of these depict different modalities of training to generate different physiological effects within the user.

Many different parameters can be combined to provide different insights through the process of contextualisation. Examples of parameters include effort, resistance, biomedical, biomechanical, and environmental.

Alternate effort or cardiorespiratory parameters include heart rate or change in heart rate, heart rate variability or change in heart rate variability, respiration or change in respiration, ventilation or changes in ventilation and oxygen uptake or change in oxygen uptake. Inferred data and derivations of these parameters are also included.

Other effort parameters include speed or change in speed, power or change in power, pace or change in pace, energy expenditure or change in energy expenditure, acceleration or changes in acceleration and muscle contraction via electromyography or changes in muscle contractions. Limb turnover like stride rate, stroke rate and cadence can also help infer effort. Derivations of these parameters are also included.

Resistance parameters include environmental forms of resistance like altitude or a change in altitude, slope or change in slope, gradient or change in gradient, incline or change in incline. Derivations of these parameters are also included.

Other resistance parameters include body weight and carried weight or changes in body weight or carried weight and lifted weight or changes in a lifted weight. Derivations of these parameters are also included.

Biomedical parameters include body temperature or change in body temperature, blood pressure or a change in blood pressure, patterns in Electrocardiograph data on changes in patterns occurring in Electrocardiograph data, oxygen saturation or changes in oxygen saturation, blood glucose or changes in blood glucose, blood cholesterol or changes in blood cholesterol and EEG or changes in EEG. Also included are hydration levels and changes in hydration levels. Derivations of these parameters are also included.

Biomechanical parameters include vertical oscillation during walking or running, foot strike impact, time on the ground, and foot strike patterns. Derivations of these parameters are also included.

Environmental condition parameters include ambient temperature, relative humidity, barometric pressure, heat index, local wind speed, local wind direction, local rain, local altitude or changes in ambient temperature, relative humidity, barometric pressure, heat index, local wind speed, local wind direction, local rain, local altitude. Derivations of these parameters are also included.

In summary, Activity Type Classification is very distinct from Training Zones in that Training Zones are only an aspect of Activity Types. True analysis, interpretation, coaching advice and modification of an Activity Plan cannot occur accurately, safely and effectively without Activity Types and classification of training with the use of them. In the four decades that Portable Biometric Data Measurement companies (like Polar, Timex, Garmin and Suunto) have been around this distinction has not been made.

3.2 Multi Parameter Classification of Activity: Activity Types

The classification system enables activity session data to be classified into one or more activity types. The classification system has knowledge of one or more activity types and their specific relationship with one or more parameters to achieve this. This knowledge may be simple or complex based on the application and desired accuracy of the system. Generally, one or more threshold criteria such as values or zones associated with each parameter related to a particular activity must be satisfied for that activity to be performed. In other words, an activity can be identified by the classification system when every threshold criteria is satisfied for each of a combination of parameters that define that activity. In the preferred embodiment the classification system uses multiple parameters to define activities.

An activity may be identified from different combinations of parameters. This diversifies the compatibility of the system with different monitoring devices. For example, an 'easy walking' activity may be defined by a stride rate threshold (such as less than 60 steps per minute) and a terrain threshold (such as a gradient of less than 2°), or a speed threshold (less than 8 km/hr) and a terrain threshold (gradient of less than 2°), or a heart rate threshold (such as between 40 and 110 beats per min) and a terrain threshold (such as a gradient of less than 2°). This allows for different types of special purpose monitoring devices to be used alongside the system. For instance a mobile phone with GPS capability for measuring speed can be the monitoring device, or a more advanced device can be used for measuring heart rate and other parameters such as speed, altitude, distance, time and turnover (e.g. stride rate).

3.3 Compliance to Activity Plan and Performance Measures

Comparisons of classified data segments can be made in 2 ways; compliance with the planned workout that they are completing or have completed and performance measures using physiological, biomechanical and strategy performance assessments of the activity data compared to historic values previously obtained in other past workouts.

Compliance involves calculating the difference between the training completed and the Activity Plan and putting the value of the difference against a set of thresholds and where the value conforms to a threshold coaching advice or a plan modification is elicited.

Performance involves applying a number of interpretative performance assessment algorithms to the data in an Activity Type segment. These algorithms involve assessing Endurance, Strength Endurance and Speed and also includes an Overall Performance assessment based on combining and summarising the other 3 performance values. These performance values for an Activity Type data segment can then be compared to historic performance values for the same categories for the average of the most recent 6 data segments for the same Activity Type. The difference between the current values for Endurance, Strength Endurance, Speed and Overall Performance and their historic values is calculated. These differences are then applied to a set of thresholds and where the value conforms to a threshold coaching advice or an Activity plan modification is elicited.

3.4 Prescription—Automated Coaching Advice for User Behavior Modification

Coaching Advice has 2 components. A detection or acknowledgement aspect and a solution aspect. The detection or acknowledgement sets the context for the coaching advice. Examples like "Cardiovascular Fatigue detected" and "too hard in warm up" explain what the system has detected but provides no actual advice on how to improve the situation. The coaching advice means that the system will then provide a solution to the problem detected. So in the above examples the coaching commentary would be; "Cardiovascular Fatigue detected, all speed training and hill work cancelled, cut the workout short so you can recover", and "too hard in warm up", can be solved by the coaching advice; "slow down to an Easy exercise effort, starting too hard can lead to injury."

Coaching advice mainly covers technique, compliance and performance issues.

3.5 Prescription—Automated Workout or Activity Plan Modification

Plan adjustment can occur in 2 different ways and 2 different times. The 2 ways that can occur is that a single workout or activity session can be modified or a complete Activity Plan can be modified. The 2 different times that this can occur over is in real time or once the workout is complete.

Workout adjustments usually occur in real time and Activity Plan adjustments usually occur once the workout has been completed.

Real time workout modifications involve changing the duration of the workout, the number of instances each Activity Type occurs within the workout, the durations or distances of the Activity Type, the rest durations between Activity Types, the number of vertical meters climbed on hills during a workout and some of the parameters used to define an Activity Type.

Post workout Activity Plan modifications adjust all or some of the planned workouts into the future as scheduled by the Activity Plan. Workout durations and Activity Type durations are usually linked into progressions through the Activity Plan into the future. The adjustment can be for the progressions of workout volumes and/or the volumes of the Activity Types. The volumes may be distance, duration or instances of an Activity Type. This means that all the components of the Activity Plan and Workout are fully flexible and can be automatically and dynamically updated.

Preferred Embodiment(s)

The system and method of the invention may be implemented using the following classification system. This implementation should not be considered as limiting the scope of the invention but rather a preferred embodiment of the underlying classification concept defined above.

4. Activity Types: Multi Parameter Classification of Activity 4.1 Minimum Activity Classification Example The following is a list of the minimum activities to be classified by the classification system of one embodiment of the invention. The following example uses running Activity Types:
  a. Easy Activity Type: This is running within the speed thresholds of 8-10 km/hr. In this example the threshold criteria for effort may include heart rate instead of speed which would be a user heart rate (HR) of 65-75% of their maximum heart rate. Power may also be used. In addition to any combination of the above parameters and their threshold criteria, a flat terrain criterion may be required by the classification system. In this case, the system may define a flat terrain for easy running as an upward or downward slope of less than 2° (or 4% gradient where consistent altitude
  b. Hills—This activity occurs when an individual increases their altitude during exercise/activity. The threshold criteria required to classify an activity under Hills can be a continuous rise over time that exceeds a 6 meter vertical gained from the flat, or a continuous slope of 2° for more than 10 secs. A Rolling Hill would be a climb of more than 6 meters but less than 20 meters and a Hill would be more than 20 m.
  c. Speed The threshold criteria for such a parameter may be a user heart rate (HR) of more than 75% of their maximum heart rate. Effort may alternatively or in addition be measured using speed and/or power In addition to any combination of the above parameters and their threshold criteria, a flat terrain criterion may be required by the classification system to identify a speed activity. In which case, the system may define a flat terrain for speed as an upward or downward slope of less than 2° (or 4% gradient). One possible Activity Type includes Up Tempo as described with Anaerobic Threshold being a slightly higher intensity.

There are different ways to classify an activity. Any combination of parameters such as speed, heart rate, power, turnover, distance per turnover, R-R (HRV), vertical meters ascended, slope, gradient can be used to depict a particular classification. Furthermore, there can be many ways to define the threshold or zone for each of these using a maximum value tested or obtained from within training or activity, using the Anaerobic or Aerobic Threshold value, or using averages based on the activity or exercise of the user etc.

The above monitored parameters and in particular the threshold criteria are only exemplary and reflect possible embodiments of the invention. They are not intended to be limiting. It is preferred in fact to have variations on the threshold criteria (and zones) for each individual as the system may be calibrated to their specific ability and needs.

4.2 Detailed Activity Classification—Parameters that Make Up Activity Types

The monitored parameters aid the system in identification and classification of activities performed during the exercise session, as each activity is defined by one or more threshold criteria (i.e. threshold values or zones) associated with one or more parameters.

In the preferred system associated with the activities it is preferred to have a resistance parameter and more preferably an intensity/effort parameter also.

For most activities like running, cycling, walking, horse training, and activity status monitoring categories the activities can be defined by the system using a resistance parameter and an effort parameter measured over time or distance. The measure of effort is preferably defined using speed, heart rate or power (a direct measure or one derived from speed, body weight and slope). It can also use respiration rate, force and acceleration. Resistance parameters can be defined by changes in altitude, slope or gradient.

For rowing and kayaking, there is no terrain component so a turnover parameter (e.g. stroke rate) or distance per limb turnover (e.g. distance per stroke) is preferably used by the system in its place.

The turnover parameter may also be used as the resistance parameter (instead of or in conjunction with terrain) to identify cycling activities.

For health or environmental monitoring, the classification is the incidence of a health (ECG, Blood Pressure) or environmental (Temperature, Heat Index, Wind Speed) parameter matched up to the other parameters that describe a situation (heart rate, terrain, speed etc).

It is preferable that the system caters for more parameters as this would enhance the flexibility of the system not just with accuracy and the ability to define more activities but also in terms of compatibility with different special purpose monitoring devices. A list of other possible additional parameters is shown below.
  1. Duration
  2. Distance
  3. Location
  4. 'Turnover' (stride rate, cadence, stroke rate)
  5. Distance covered per Turnover
  6. Positional Status (is the person upright or lying down)
  7. ECG
  8. Blood Pressure
  9. Ambient temperature
  10. Relative Humidity
  11. Barometric Pressure
  12. Heat Index
  13. Local Wind Speed & Direction
  14. Local Rain 15. Some derived combinations (e.g. watts/kg)
16. Body Weight
17. Personal Gear—Carried Weight (e.g. tramping pack)
18. Jumping—vertical (varying heights)
19. Jumping—horizontal (varying distances)
20. Drop
21. Climbing
22. Crawling
23. Direction (heading)
24. Oxygen uptake
25. Respiration
26. Ventilation
27. Energy Expenditure
28. Energy Intake
29. Blood Pressure
30. ECG
31. R-R (HRV)
32. Body Temperature
33. Current weather
34. Degree of Movement
35. On the ground
36. Direction the user is facing or moving (forwards, backwards, sideways)

5. Compliance to Activity Plan and Performance Measures Interpretation Model

Apart from Activity Types classification another component is required for accurate interpretation and coaching prescription. This is the use of interpretative algorithms to drive modifications of future Activity Types within an Activity session or long Term Plan. The two most interpretative measures of the Activity Type segments are compliance and performance measures.

Compliance measures detect how closely a user has followed an Activity session plan in terms of completion of prescribed Activity Type segments; their durations or distances, intensities, number of instances and rest periods between Activity Types.

Physiological performance assessments can be applied to the Activity Type data segments to assess an improvement, a static state or deterioration in physical ability. The physiological performance assessments assess different aspects of a user's ability within the Activity Type data segment. These performance measures can include cardiovascular, neurocardio, muscular and overall performance measures.

Cardiovascular measures include derived algorithms that use heart rate and respiration which may or may not include other parameters. Neurocardio measures include measures and derived algorithms of heart rate variability which may or may not include other parameters. Muscular measures and derived algorithms include power, acceleration and force along which may or may not include other parameters. Overall performance measures and derived algorithms include power and speed which may or may not include other parameters.

The state of the art has developed where many performance type measures such as EPOC or Training Effectiveness can be applied to heart rate data to adjust training volumes but these systems do not assess muscular ability, cannot provide coaching advice around Activity Types and cannot adjust the Activity Types within an activity or training session. The Activity Type factors that could be adjusted are Activity Type duration, number of instances of an Activity Type, rests between Activity Type instances and adjustments of the parameters that make up the Activity Type.

The state of the art also includes other performance measures like Training Stress Score, Acute Training load, Chronic Training Load, Heart Rate Variability, VO2max and Exercise Economy measures to either infer performance or provide some insight into a user's current physiological status. These measures however do not provide any interpretive solution to what the measures mean to a user and how they should modify their activities going into the future whether they be a modification of Activity Type segments in future Activity sessions or coaching advice about modifications in the users behaviour going into the future.

The combination of Activity Type Classification, Activity Plan Compliance and Physiological Performance assessment provides an opportunity to provide genuinely accurate automated coaching to users.

Technique measures may also be used.

Coaching Advice and Activity Plan Modification occur where a plurality of values are able to be derived from Activity Type Classifications. These values include Compliance Values and Performance Measures for Activity Types.

Raw and Derived Data Parameters

Raw and derived data for some of the possible measures are described below:

5.1 Compliance:

Duration: Duration is the number of minutes a classified Activity Type segment occurs for or the accumulated time for Activity Type segments of the same label. (e.g. one segment of Up Tempo might be 2 mins long or three segments of Up Tempo might add up to 5 mins and 20 seconds)

Number of Repetitions completed: This is a count of the number of Activity Type segments that have begun and stopped during an activity session. (e.g. the system may have detected the Up Tempo Activity Type 5 times during the workout while the user was training so the number of repetitions (reps) completed was 5.)

Number of Hills completed: This is a count of the number of hill segments detected and completed within a workout. Rolling Hills are detected by a continuous increase of more than 6 meters and less than 20 meters and Hills are detected as an increase of more than 20 meters as covered by the Activity Classification Method. Counting the number of Hills is multi parameter because the system needs to know that the user is not only climbing a Hill but also running.

Cumulative Vertical Meters Ascended: This is a measure of the number of meters ascended over an entire workout for Rolling Hills and Hills independently. (e.g. Rolling Hills could involve 3 climbs; the first being 15 meters, the 2nd being 15 meters and the 3rd being 10 meters which means a cumulative vertical meters ascended for Rolling Hills of 40 meters.)

Many other possible areas are able to be measured within the bounds of performance, technique and compliance.

5.2 Performance:

Performance involves several algorithms to determine performance changes on a day to day basis.

The areas of assessment are Endurance, Strength Endurance and Speed. These are then scored and combined to provide an overall performance measure and to provide indications of 'coaching advice' and 'plan modification'.

Endurance: Endurance measures cardiovascular fitness.
Strength Endurance: Strength Endurance measures muscular endurance fitness.
Speed: Speed measures the ability to combine Endurance and strength endurance.

The determination of each performance algorithm is based on combinations of the following parameters: heart rate, weight, speed, distance, limb turnover (e.g. cadence, stride rate, stroke rate), distance per limb turnover (e.g. distance per stroke, stride length) time, power, and altitude, slope or gradient change.

Technique measures may also be used.

5.3 Sample Plan for the Workout

Below is an example of a workout that is part of a Running Activity Plan, where the workout duration and the number of reps/durations for all the Activity Types are used within the workout.

The Activity Types used in the example are:
Easy
Rolling Hills
Hills
Up Tempo
Anaerobic Threshold

| Activity Type & Workout Duration | Planned |
| --- | --- |
| Workout Duration: | 60 mins |
| Anaerobic Threshold | 0 |
| Up Tempo | 4 reps (of 4 mins) |
| Hills | 3 hills (>20 vertical meters) |
| Rolling Hills | 0 |

The above describes a 60 min workout that has 4 periods of 4 mins of the Up tempo Activity Type in it totalling 16 mins at Up Tempo and 3 hills of greater than 20 meters making approximately 60 meters. There is no Anaerobic Threshold Speed training or Rolling Hills Activity Types to be done within the workout today.

The workout therefore uses 2 Activity Types; Up Tempo and Hills. The other 2 Activity Types are not being used; Anaerobic Threshold and Rolling Hills.

It is against this set of tasks that the user's compliance activity is measured.

Data that shows that the user followed the Activity Plan closely shows high compliance and data that does not match the plan closely enough and/or has missing tasks or tasks completed that were not scheduled within the plan will indicate poor compliance.

The following is a table of the plan versus what was actually done in the workout:

| Activity Type & Workout Duration | Planned | Actual |
| --- | --- | --- |
| Workout Duration: | 60 mins | 70 mins |
| Anaerobic Threshold (85-95% HRmax* on flat) | 0 | 0 |
| Up Tempo (75-85% HRmax* on flat) (18 mins) | 4 reps (of 4 mins) = 16 min | 3 reps |
| Hills (>20 vertical meters) | 3 hills (60 meters) | 2 hills (80 meters) |
| Rolling Hills (>6 vertical meters, <20 meters) | 0 | 0 |

*HRmax = maximum heart rate

We will now go through the analysis for each Activity Type and Total Workout duration that was specified in the plan compared to what was actually performed by the user:

6. Prescription: Automated Coaching Advice to Modify User Behaviour 6.1 Workout Duration Compliance:

The plan for the workout called for 60 mins of running. The actual exercise duration was 70 mins. The user did 10 mins more training than the program specified.

This means that the user did 116% of what they should have done for the plan. (70 mins divided by 60 mins equals 116% of the plan.)

Workout Duration Data Thresholds:
The 116% is applied against a set of thresholds
Less than 85%
85% to 95%
95% to 105%
Greater than 105%
116% fits into the 'greater than 105%' threshold.
Less than 85% "Exercise Duration was far below the plan, please follow the plan carefully"
85% to 95% "Exercise Duration was slightly below the plan, please follow the plan carefully"
95% to 105% "Exercise Duration was correct well done!"
Greater than 105% "Exercise Duration exceeded plan, please follow the plan carefully"
The coaching feedback/advice would be:
"Exercise Duration exceeded plan, please follow the plan carefully"

Timing of 'Coaching Advice'—Real Time or Post Workout:

The coaching advice for workout duration occurs immediately upon completion of the workout on a device or could be provided on a website or device for post workout feedback. A real time comment could occur however, if the workout duration is exceeded. In the example, when the users workout duration exceeds 5% greater than the prescribed workout duration of 60 mins which is 63 mins a real time comment can be given "Prescribed workout duration exceeded"

6.2 Compliance Coaching Advice:

A. Up Tempo Activity Type Compliance

The workout plan was for 4 repetitions of 4 mins making a total of 16 mins of the Activity Type; Up Tempo.

Up Tempo is an Activity Type that occurs at about 75-85% of effort. This is above the Easy Activity Type of 65-75% of effort. During a workout the runner spends most of their time at Easy but may decide to increase their effort to 75-85% of maximum heart rate to do the Up Tempo Activity Type.

Up Tempo is determined by a heart rate or speed training zone which must occur on flat terrain as per the classification description. 75-85% of maximum might equate to a heart rate of 175-185 bpm or a speed of 12.5-13.5 km/hr as calibrated by the Activity Classification method.

The runner therefore moves their effort up and heart rate reaches 175 bpm on the flat. The classification system identifies that the user has now moved into the Up Tempo Activity Type zones and will begin to log recorded data that occurs as an Up Tempo Activity Type segment. For the next 4 mins the runner focuses on keeping their heart rate within the training zone of 175 to 185 bpm on the flat. After 4 mins the user slows down again and their heart rate drops below 175 bpm which means that the user's effort has fallen out of the Up Tempo Activity Type and back into the Easy Activity Type. At this point the system discontinues logging the Up Tempo Activity Type.

Therefore the logged duration of the Up Tempo Activity Type segment is 4 mins.

In this case the user incorrectly logged Up Tempo 3 times as opposed to the 4 repetitions that were planned within the workout. There were correct and incorrect rep durations of 4 mins, 11 mins and 3 mins making a total of 18 mins.

Up Tempo Compliance Utilizes 2 Measurement Areas:
Up Tempo Duration
And repetitions completed
Up Tempo Duration Data Calculation:
The planned workout duration for Up Tempo was 16 mins and 18 mins was completed during the workout.

18 mins divided by 16 mins equals 112% meaning that 12% more Up Tempo Duration training occurred than was planned.

Up Tempo Duration Data Thresholds:

| (=>, <) | | Takes most significant comment (i.e. Compliance: <−1.5% or >1%, performance: <−2% or >0.2%, if 2 significant comments split (hi/lo, lo/lo, hi/hi) = most % biggest change. |
|---|---|---|
| 1 | <−2% | Part of going fast is getting used to the speed. Up Tempo is used to aid you in acquiring speed endurance. Look at the duration targets in the plan more carefully. |
| 2 | (−2% to −1%) | You can't get faster without speed and Up Tempo is a good low impact way to do this. Use the training program for guidelines on how much you should do. |
| 3 | (−1% to 1%) | Good work! |
| 4 | 1% to 5% | Too much speedwork is a bad thing. Apart from increasing chance of injury, it causes high fatigue, upsets your energy for other workouts and can predispose you to illness. |

The correct coaching advice for 12% more for Up Tempo Duration training done than scheduled is 4 (see table above):

"Too much speedwork is a bad thing, apart from increasing chance of injury, it causes high fatigue, upsets your energy for other workouts and can predispose you to illness."

Up Tempo Repetitions Completed Data Calculation:

The plan was for 4 repetitions of 4 mins at Up Tempo and the actual training carried out—was 3 repetitions of 4 mins, 11 mins and 3 mins.

4 repetitions were supposed to be completed and only 3 were completed.

3÷4=75% meaning −25% less Up Tempo Repetitions completed occurred than planned.

Up Tempo Repetitions Completed Data Thresholds:

| 1 | <−2% | You need to progressively increase the number of reps of a training type that you do to get improvement. The training program will guide you on this. |
|---|---|---|
| 2 | (−2% to −1%) | To get faster there has to be some increase in the number of reps run for this training type within a workout. |
| 3 | (−1% to 1%) | Nice work, keep moving the number reps of Up Tempo run up gradually over time. |
| 4 | 1% to 5% | If you didn't plan to do extra Up Tempo, you might be pushing it a little hard as you seem to be jumping up into Up Tempo too often. |

The correct coaching advice for −25% Up Tempo Reps Completed is 1 (see table above):

"You need to progressively increase the number of reps of an Activity Type that you do to get an improvement. The training program will guide you on this."

Timing of 'Coaching Advice'—Real Time or Post Workout:

Coaching feedback can occur in real time if the user exceeds the total duration of up tempo scheduled in the plan. The following advice would be given: "Too much Up Tempo speedwork, this can overtrain you or cause injury. Discontinue Up Tempo training." This would occur immediately after the planned Up Tempo duration is exceeded by more than 5% of the planned duration for the Up Tempo Activity Type. For 4 repetitions of 4 mins making 16 mins of the planned Up tempo, a 5% increase is 16.8 mins or 16 mins 48 secs.

If the duration for a particular rep is exceeded by more than 10% which for a 4 mins repetition is 4.4 mins or 4 mins 24 secs, the commentary is "Planned Rep duration exceeded, slow down" and if the planned duration matches within + or −10% (e.g 4 mins+/−24 secs) the real time comment is "Excellent, your rep duration was correct". If the rep duration is less than −10% (e.g. 3 mins 36 secs) the comment is: "Rep Duration too short"

After the completion of each repetition, a data summary is provided which includes the duration of the repetition. For example at the end of the repetition of Up tempo the commentary is: "$1^{st}$, $2^{nd}$, etc Up Tempo Rep Completed Xmins"

B. Hills Activity Type Compliance:

The workout plan was for 3 Hills which means a minimum of 60 vertical meters ascended is planned.

Hills are measured if the continuous ascent for a user travelling faster than 7 km/hr exceeds 20 meters of continuous climbing. 3 Hills means a minimum of 60 vertical meters ascended. The user runs to the hill and after 6 meters of vertical ascent a hill is detected, when the user exceeds 20 meters the Activity Type is classed as Hills Activity Type and is logged as such until the user reaches the top at say 27 meters. When the user reaches the top and the terrain plateaus, the system detects that the user has stopped climbing.

At this point the system discontinues logging the Hills Activity Type.

Therefore, the logged vertical meters ascended is in this case 27 meters for a Hills Activity Type segment.

The user incorrectly logged 2 hills totalling 80 vertical meters of climbing, 1 of 27 meters and the other of 53 meters.

Hills Compliance Utilizes 2 Measurement Areas:

Number of Hills Completed

And Cumulative Vertical Meters Ascended

Number of Hills Completed Data Calculation:

The planned number of hills was 3 and only 2 hills were completed.

2÷3=66% or −34% less hills than planned.

Number of Hills Completed Data Thresholds:

| (=>, <) | | Takes most significant comment (i.e. Compliance: <−1.5% or >1%, performance <−2% or >0.2%, if 2 significant comments split (hi/lo, lo/lo, hi/hi) = most % biggest change. |
|---|---|---|
| 1 | <−2% | Without a steady increase in your hill work, you don't get the stiumlus that drives your strength endurance up. Increase the number of hills you do gradually each session. |
| 2 | (<2% to −1%) | To get stronger, you need more load and in this case that means slightly more hills each time you do a hills session. |
| 3 | (−1% to 1%) | Great Work! |
| 4 | >1% | Overdoing your training is not beneficial, it is more likely to lead to injury, illness or fatigue. Follow the training plan more closely please. |

The correct coaching advice for −34% less Hills completed than scheduled is 1 (see table above):

"Without a steady increase in your hill work you don't get the stimulus that drives your strength endurance up. Increase the number of hills you are doing gradually each session."

Cumulative Vertical Meters Ascended Data Calculation:

The plan was for approximately 60 vertical meters of climbing to be done and 80 vertical meters was climbed.

80÷60=133% meaning 33% more meters climbed than planned.

Cumulative Vertical Meters Ascended Data Thresholds:

| | | |
|---|---|---|
| 1 | <−2% | To get an improvement in your strength endurance you need more load and in this case it means slightly more climbed vertical meters each time you do a hills session. |
| 2 | (−2% to −1%) | Getting stronger strength endurance wise is not made without some increase in the volume of meters climbed in training. |
| 3 | (−1% to 1%) | Nice work, keep building on the number of vertical meters ascended you do gradually over time. |
| 4 | >1% | Doing more climbing than is in the training plan is counter productive, you are far more likely to disrupt the balance of the program, get fatigued or worse injured. Follow the plan. |

The correct coaching advice for 33% more vertical meters climbed than was planned for Hills is 4 (see table above):

"Doing more climbing than is in the Activity Plan is counterproductive, you are far more likely to disrupt the balance of the program, get fatigued or worse, get injured. Follow the plan."

Timing of 'Coaching Advice'—Real Time or Post Workout:

Coaching feedback can occur in 'real time' if the user exceeds the vertical meters of the Hills scheduled in the plan by 20% or more (60×120%=72 meters). If the user did 72 meters or more then the following advice would be given: "Too much Hill work, this can overtrain you or cause injury. Discontinue Hill Training" This would occur immediately after 72 meters was exceeded.

At the completion of each Hill a data summary is provided which includes the vertical meters climbed and the number of Hills climbed to that point. For example at the completion of the $1^{st}$ Hill of 27 meters the commentary is: "$1^{st}$ Hill completed, 27 meters, Cumulative Vertical Meters: 27 meters."

C. Easy Activity Type Compliance

All training that is not Up Tempo, Anaerobic Threshold, Rolling Hills or Hills is classed as Easy Activity Type. As the user goes through a workout they will complete other Activity Type. In this case the user did 3 repetitions of 4, 11 and 3 mins of Up Tempo and 2 Hills totalling 80 meters. In between each of these Activity Types the user was still running and the default Activity Type is Easy. Therefore multiple segments of the Easy Activity Type were produced in this workout. If we include a warm up and a warm down and count Easy segments between other Activity Types the number of Easy Activity Type segments is 6.

The compliance for the Easy Activity Type is not measured, as Easy is the default that occurs in between the other Activity Types.

Compliance Count Ups:

An assessment of what Activity Types needs to be completed during the workout is made every 20 mins. This means that the system works out what scheduled training has been completed and what has not been completed allowing the user some explanation of what is left to train. Because the classification system outlined previously can automatically detect an Activity Type, it allows the user to do Activity Types when it is most suitable so it is useful to be informed of what Activity Types are left to train as the user moves through the workout. For example, after 20 mins of training the user may have completed 1 repetition of Up Tempo and have completed 1 Hill. The system analyses this against the plan of 4 Up Tempo repetitions and 3 Hills and the comment is "Training to complete; 3 Up tempo and 2 Hills, Time: 20 mins."

Figure 6:
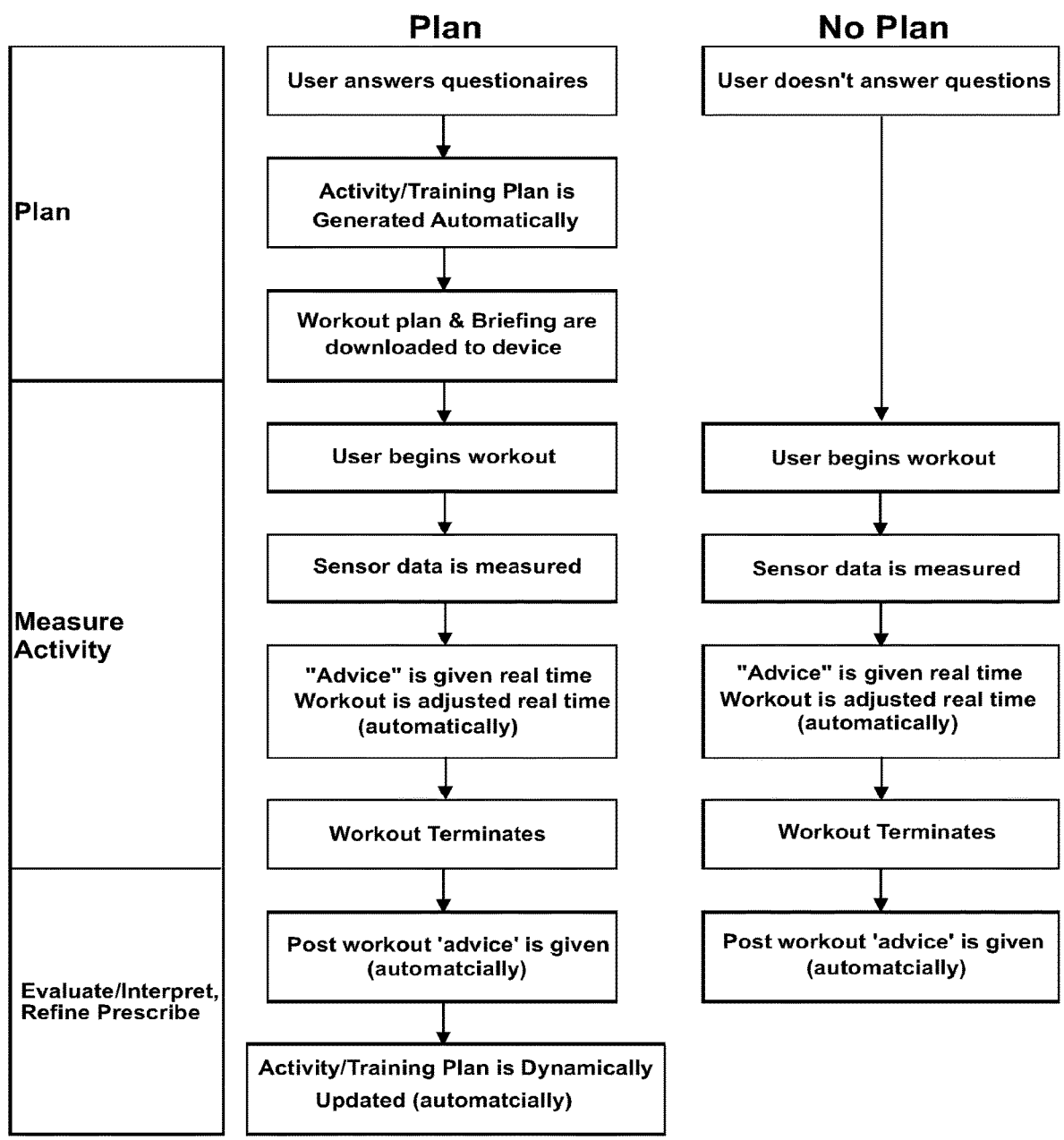
FIG. 6 shows the steps in the Virtual Coaching system when a user uses an exercise Activity Plan and when no exercise Activity Plan is used.
Figure 7:
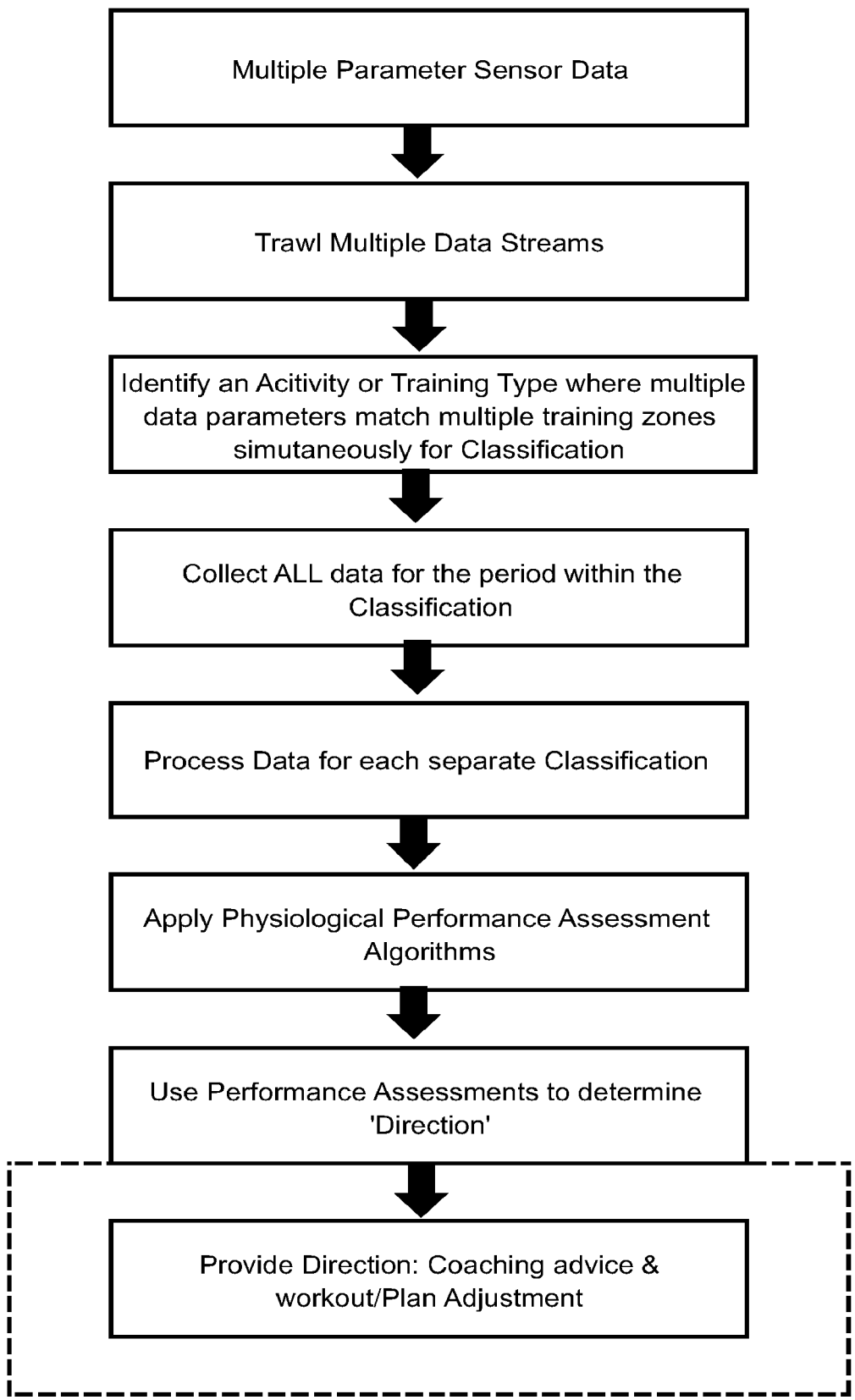
FIG. 7 shows the steps in the Virtual Coaching system and the Coaching 'Prescription' aspect of the system.

6.3 Performance Coaching Advice:

Performance measures provide feedback to the user on improvement and fatigue and these physiological performance assessments drive coaching prescription. (see FIGS. 6 & 7) If performance values are increasing the user is improving. If performance values are dropping despite careful compliance to the plan, the user is either fatigued or ill.

Figure 8:
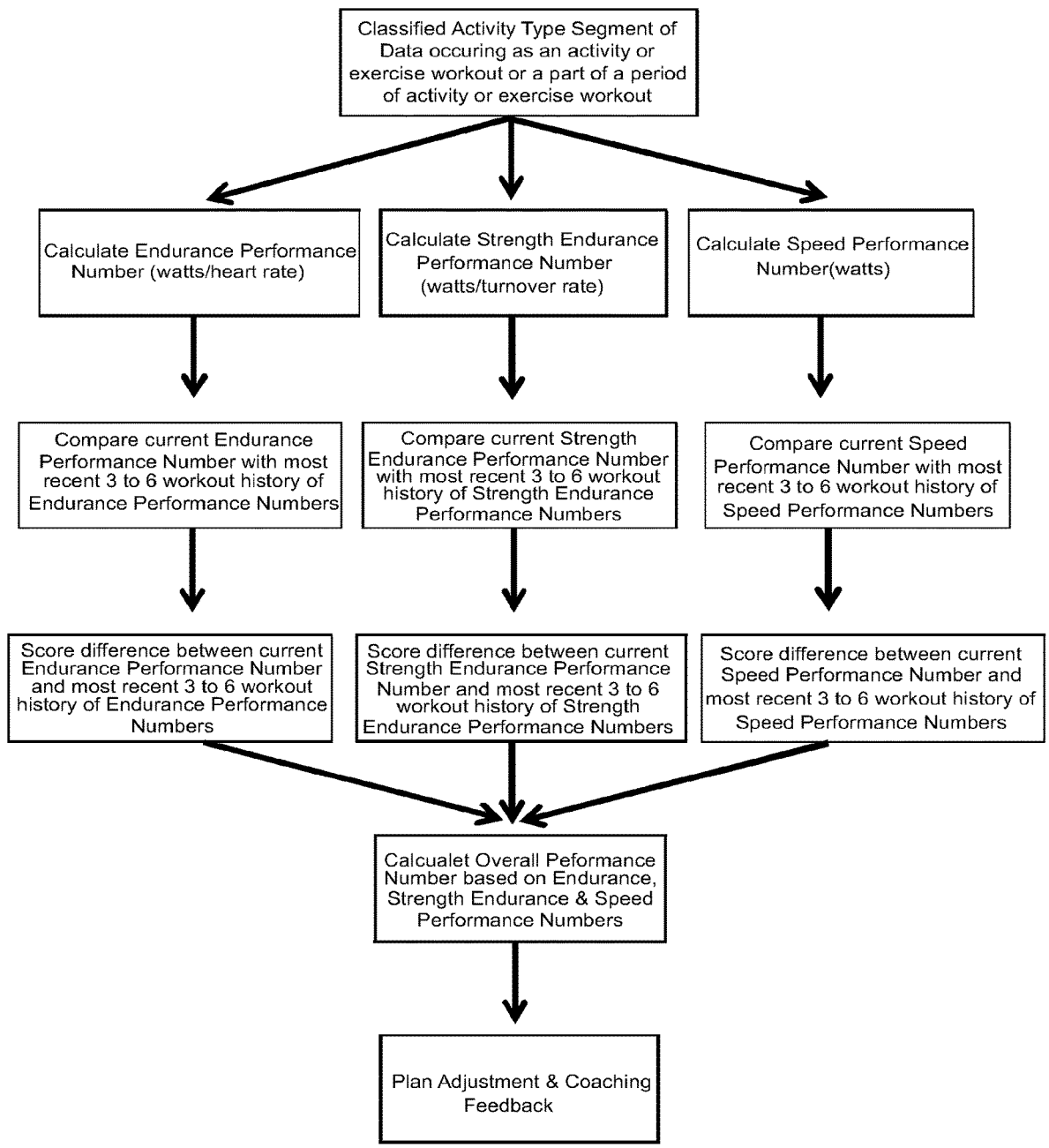
FIG. 8 shows the detailed steps of the physiological performance assessment system

Performance values can be broken into 3 components and calculated by the Performance Engine: (see FIG. 8)

Endurance Performance—performance of the cardiovascular system ('puff')

Strength Endurance Performance—performance of the muscular system ('strength')

Speed Performance—performance of power ('strength moved fast')

Each performance value is measured individually for each Activity Type but they are also combined to provide an overall performance measure.

Performance is measured for each Activity Type independently. Therefore performance is measured for:

Easy
Rolling Hills
Hills
Up Tempo
Anaerobic Threshold

The method involves applying raw or derived data to a series of thresholds that are linked to coaching advice. A score is also generated.

Performance values are measured specific to their Activity Type. This means that only Up Tempo Activity Type segments can be compared with other historic Up Tempo Activity Type segments.

Other Activity Types like Hill Activity Type performance would also be compared against their own historic segments.

Performance Values are separated this way to allow for some level of independent measurement of each of the key Activity Types that make up an individual's physiology for the sports and activities analysed. This means that based on the 3 measured performance areas, strengths and weaknesses can be identified allowing the Activity Plan to be more personalized to the individual which would not be possible with a single all-encompassing measure.

Performance measures are very important in that they drive the changes in the plan in relation to the user's physiological adaptations. This can happen in 2 ways; it can change a workout or on a broader level it can change the makeup of an Activity Plan.

In terms of a workout or several workouts following along through a week, if strength endurance has deteriorated this will be an indication of muscular fatigue and the strength endurance Activity Types of Rolling Hills and Hills will be reduced or eliminated depending on the severity.

Speed Activity Types of Up Tempo and Anaerobic Threshold will also be reduced.

A drop in Endurance levels indicates cardiovascular fatigue which will require a reduction of the total workout volumes and in more severe cases, a reduction in all Activity Type volumes as well.

Speed deterioration may mean reducing speed Activity Type volumes. Higher values in all 3 performance parameters means improvement either through recovery or physiological improvement. Several performance parameters may change simultaneously leading to multiple adjustments of the above.

From a long term plan adjustment point of view, a low Strength Endurance measure might mean more Hills and Rolling Hills Activity Types are required in the plan.

Low Speed values and high Strength Endurance values might mean more speed training like the Up Tempo and Anaerobic Threshold Activity Types and less Strength Endurance Activity Types are required in the plan.

Low Endurance values might mean forgoing Strength Endurance and Speed Activity Types in favour of just doing easy training using the Easy Activity Type.

Performance measures are always compared with the individuals own past historic data.

A. Up Tempo Performance

As a user carries out Up Tempo training, streams of data during that time are identified, logged and labelled as Up Tempo. At the same time a number of physiological processes are occurring and performance measures can be taken.

Up Tempo performance is measured using algorithms for:
Endurance
Strength endurance
Speed
Up Tempo Endurance, Strength Endurance and Speed are all used to analyse Up Tempo.

Endurance Performance Analysis for Up Tempo

The Endurance performance value is determined based on the data streams within an Activity Type segment of a workout or across the accumulation of all segments for a particular Activity Type within a workout or session.

The Endurance performance value is determined and then compared to the historic average value for the same calculation for Up Tempo in the last 3 workouts where Up Tempo occurred. (In the last 2 weeks)

This shows a 0.8% increase.
Endurance performance improved by 0.8%.
Up Tempo Endurance Thresholds:
Post Workout Combined Segments for Up Tempo Activity Type:

| | (=>, <) | Takes most significant comment (i.e. Compliance: <-1.5% or >1%, performance: <-2% or >0.2%, if 2 significant comments split (hi/lo, lo/lo, hi/hi) = most % biggest change. |
|---|---|---|
| 1 | <-2% | Miss your next workout, and easy, no speed for the following session. You can't have lost fitness, low heart rates for the next 2 workouts to help your 'puff' recover. |
| 2 | (-2% to -1%) | Slight cardiovascular fatigue, rest up well before your next workout so that you are fresh enough to do it. |
| 3 | (-1% to 1%) | No comment. |
| 4 | >1% | Endurance improved. You are managing the endurance aspects of your training well by allowing enough recovery between high heart rate workouts. |

The post workout coaching advice for 0.8% is therefore 3 (see table above): no comment.

Real Time Individual Segment for Up Tempo Activity Type:

| | (=>, <) | Takes most significant comment (i.e. Compliance: <-1.5% or >1%, performance: <-2% or >0.2%, if 2 significant comments split (hi/lo, lo/lo, hi/hi) = % biggest change. |
|---|---|---|
| 1 | <-2% | Cancel all remaining Up Tempo Training, you are too cardiovascularly fatigued. |
| 2 | (-2% to -1%) | Some cardiovascular fatigue detected. Take it easy, don't push the Up Tempo too hard. |
| 3 | (-1% to 1%) | No comment. |
| 4 | >1% | You have improved, nice work! |

By way of example let us assume that the real time coaching advice was −1.4% for the 2nd and 3rd Up Tempo Repetitions within the workout which is therefore 2 (see table above) so the coaching advice would be: "Some cardiovascular fatigue detected, take it easy, don't push the Up Tempo too hard"

Scoring Interpreted Data:

| <-3% | (-3% to -2%) | (-2% to -1.3%) | (-1.3% to -0.5%) | (-0.5% to 0.2%) | 0.2% to 1.3% | 1.3% to 2.3% | 2.3% to 3.4% | 3.4%-5% | >5% |
|---|---|---|---|---|---|---|---|---|---|
| 1 | 2 | 3 | 4 | 5 (=>, <) | 6 | 7 | 8 | 9 | 10 |

At the end of the workout, the post workout value is for 0.8% is a score of 6 (see table above).

Timing of 'Coaching Advice'—Real Time or Post Workout:

The coaching advice can be given immediately after the Up Tempo segment during the workout in real time; "Some cardiovascular fatigue detected, take it easy, don't push the Up Tempo too hard" At the end of the workout a comment is provided specific to the Up tempo Activity Type; "Slight cardiovascular fatigue, rest up well before your next workout so that you are fresh enough to do it."

Strength Endurance Performance Analysis for Up Tempo:

From the many streams of data logged for the 18 min of Up Tempo, a Strength Endurance value was determined.

This was compared to the historic data for the user and a 1.2% decrease (−1.2%) in strength endurance performance is measured.

Up Tempo Strength Endurance Thresholds:
Post Workout Combined Segments for Up Tempo Activity Type:

| 1 | <-2% | You have high muscular fatigue, try to rest your legs up before the next workout & take it easy with the Rolling Hills & Hills traning. |
|---|---|---|
| 2 | (-2% to -1%) | You have mild muscular fatigue, take it easy with the muscular aspects of the next workout. |
| 3 | (-1% to 1%) | No comment. |
| 4 | >1% | Excellent, keep it up! Your legs are getting stronger! |

The post workout coaching advice for −1.2% is therefore 2 (see table above) which is: "You have mild muscular fatigue, take it easy with the muscular aspects of the next workout" Real Time Individual Segment for Up Tempo Activity Type:

| 1 | <−2% | Cancel all remaining Up Tempo reps, you are too muscularly fatigued. |
| 2 | (−2% to −1%) | Some muscular fatigue detected. Take it easy, don't push the Up Tempo too hard. |
| 3 | (−1% to 1%) | No comment. |
| 4 | >1% | You are stronger, nice work! |

By way of example let us assume that the real time coaching advice was −1.2% for the 3rd Up Tempo Repetition within the workout. This is therefore 3 (see table above), so the coaching advice would be: "Some muscular fatigue detected, Take it easy, don't push the Up Tempo too hard."

Scoring Interpreted Data:

| <−3% | (−3% to −2%) | (−2% to −1.4%) | (−1.4% to −0.5%) | (−0.5% to 0.2%) | 0.2% to 1.4% | 1.4% to 2.3% | 2.3% to 3.4% | 3.4%-5% | >5% |
|---|---|---|---|---|---|---|---|---|---|
| 1 | 2 | 3 | 4 | 5 (=>, <) | 7 | 8 | 9 | 10 | 10 |

At the end of the workout the value was −1.2% which scores 4 (see table above).

Timing of 'Coaching Advice'—Real Time or Post Workout:

The coaching advice can be given immediately after the Up Tempo segment during the workout in real time which in this case would be: "Some muscular fatigue detected, Take it easy, don't push the Up Tempo too hard"

Commentary can also be provided post workout.

Speed Performance Analysis for Up Tempo

The Speed performance value was determined and compared to historic data and a 2% increase in Speed performance ability was obtained Up Tempo Speed Thresholds:

Post Workout Combined Segments for Up Tempo Activity Type:

| 1 | <−2% | Work on controlling the intensity of your training better so you don't get too tired! Don't go too hard. You have to be fresh enough so you can get the most |
| 2 | (−2% to −1%) | You might need to think about whether you are training too fast or hard in easy, try backing the effort off a little. |
| 3 | (−1% to 1%) | No comment. |
| 4 | >1% | You showed a speed increase during Up tempo training today! |

The post workout coaching advice for 2% is therefore a score of 4 (see table above) which is: "You showed a speed increase during Up Tempo training today."

Real Time Individual Segment for Up Tempo Activity Type:

| 1 | <−2% | Cancel all remaining Up tempo training, you are too slow and fatigued. |
| 2 | (−2% to −1%) | Some fatigue detected. Take it easy, don't push the Up Tempo too hard. |
| 3 | (−1% to 1%) | No comment. |
| 4 | >1% | You are faster, nice work! |

The real time coaching advice was 0.8% for the 1st Up Tempo Repetition within the workout which scores 4 (see table above) so the coaching advice would be: "You are faster, nice work!"

Scoring Interpreted Data:

| <-3% | (-3% to -2%) | (-2% to -1.3%) | (-1.3% to -0.5%) | (-0.5% to 0.2%) | 0.2% to 1.3% | 1.3% to 2.3% | 2.3% to 3.4% | 3.4%-5% |
|---|---|---|---|---|---|---|---|---|
| 1 | 2 | 3 | 4 | 5 (=>, <) | 7 | 8 | 9 | 10 |

The post workout value is 2% which gives a score of 8. (see table above)

Timing of 'Coaching Advice'—Real Time or Post Workout:

The coaching advice can be given immediately after the Up Tempo segment during the workout in real time; "You are faster, nice work!" or post workout to provide specific advice on the Up Tempo segment which would be; "You are managing your training extremely well & your speed is increasing. Congratulations."

The method for Anaerobic Threshold analysis is exactly the same as Up Tempo analysis.

B. Hills Performance

Endurance Performance Analysis for Hills

Hills only use strength endurance and endurance for analysis. Speed is not relevant to Hill training.

Endurance Performance values were determined both within Hills segments and over the combined segments. Endurance performance for Hills showed a 1.4% decrease. (-1.4%) Hills Endurance Thresholds:

Post Workout Combined Segments for Hills Activity Type:

| | (=>, <) | Takes most significant comment (i.e. Compliance <-1.5% or >1%, performance: <-2% or >0.2%, if 2 significant comments split (hi/lo, lo/lo, hi/hi) = % biggest change |
|---|---|---|
| 1 | <-2% | You have high cardiovascular fatigue, you need to rest and do your easy training very gently in the next workout. Avoid speedwork. |
| 2 | (-2% to -1%) | Slight cardiovascular fatigue, go easy in the next workout. |
| 3 | (-1% to 1%) | No comment. |
| 4 | >1% | You are managing the endurance aspects of your training well by allowing enough recovery between high heart rate workouts. |

The post workout coaching advice for 1.4% scores 2 (see the table above): which is "Slight cardiovascular fatigue, go easy in the next workout"

Real Time Individual Segment for Hills Activity Type:

Real time performance is not provided because it is difficult to provide segment by segment performance measures as hill gradients change markedly.

Scoring Interpreted Data:

| <-3% | (-3% to -2%) | (-2% to -1.4%) | (-1.4% to -0.5%) | (-0.5% to 0.2%) | 0.2% to 1.4% | 1.4% to 2.3% | 2.3% to 3.4% | 3.4%-5% | >5% |
|---|---|---|---|---|---|---|---|---|---|
| 1 | 2 | 3 | 4 | 5 (=>, <) | 7 | 8 | 9 | 10 | 10 |

The post workout score for -1.4% is 3. (see the table above)

Timing of 'Coaching Advice'—Real Time or Post Workout:

Post workout commentary is provided for the Hills Activity Type.

Strength Endurance Performance Analysis for Hills:

From the many streams of data logged for the 3 hills completed, Strength Endurance values were determined.

A 2.3% decrease (−2.3%) in strength endurance performance was measured.

Hills Strength Endurance Thresholds:

Post Workout Combined Segments for Hills Activity Type:

| 1 | <−2% | You have high muscular fatigue, try to rest your legs up before the next workout & don't push the muscular aspects of the next workout too much. |
| 2 | (−2% to −1%) | You have mild muscular fatigue, take it easy with the muscular aspects of the next workout. |
| 3 | (−1% to 1%) | No comment. |
| 4 | >1% | Excellent, keep it up! Your legs are getting stronger! |

The post workout coaching advice for −2.3% is therefore 3 which is: "You have high muscular fatigue, try to rest your legs up before the next workout & don't push the muscular aspects of the next workout too much."

Real Time Individual Segment for Hills Activity Type:

Real time performance is not provided because it is difficult to provide segment by segment performance measures as hill gradients change markedly.

Scoring Interpreted Data:

| <−3% | (−3% to −2%) | (−2% to −1.4%) | (−1.4% to −0.5%) | (−0.5% to 0.2%) | 0.2% to 1.4% | 1.4% to 2.3% | 2.3% to 3.4% | 3.4%-5% | >5% |
|---|---|---|---|---|---|---|---|---|---|
| 1 | 2 | 3 | 4 | 5 (=>, <) | 7 | 8 | 9 | 10 | 10 |

The post workout score for −2.3% is 2. (see table above)

Timing of 'Coaching Advice'—Real Time or Post Workout:

Post workout commentary is provided for the Hills Activity Type.

The method for Rolling Hills analysis is exactly the same as Hills analysis.

C. Easy Performance

Endurance Performance Analysis for Easy

Easy only uses strength endurance and endurance for analysis. Speed is not relevant to Easy training.

Easy Endurance Performance was determined within Easy segments and over the combined segments.

Endurance performance for Easy increased by 0.8%.

Easy Endurance Thresholds:

Post Workout Combined Segments for Easy Activity Type:

| 1 | <−2% | You have high cardiovascular fatigue, get as much recovery as you can between workouts and you will need to train very gently in the next workout. Avoid speedwork. |
| 2 | (−2% to −1%) | You have mild cardiovascular fatigue. Take it easy in the next session to recover your cardiovascular system and then get back into it. |
| 3 | (−1% to 1%) | No comment. |
| 4 | >1% | You are managing the endurance aspects of your training well by allowing enough recovery between high heart rate workouts. |

The post workout coaching advice for 0.8% is therefore 3 (see table above) which is No comment.

Real Time Individual Segment for Easy Activity Type:

Real time performance is not provided because it is difficult to provide segment by segment performance measures because Easy segments include recovery from other forms of training that affect the performance numbers.

Scoring Interpreted Data:

| <−3% | (−3% to −2%) | (−2% to −1.4%) | (−1.4% to −0.5%) | (−0.5% to 0.2%) | 0.2% to 1.4% | 1.4% to 2.3% | 2.3% to 3.4% | 3.4%-5% | >5% |
|---|---|---|---|---|---|---|---|---|---|
| 1 | 2 | 3 | 4 | 5 (=>, <) | 6 | 8 | 9 | 10 | 10 |

The post workout score for 0.8% is 6. (see table above)

Timing of 'Coaching Advice'—Real Time or Post Workout:

Post workout commentary is provided for the Easy Activity Type. In this case there was no comment.

Strength Endurance Performance Analysis for Easy:

Strength Endurance for Easy was determined showing a 1.4% decrease (−1.4%) in Strength Endurance performance.

Easy Strength Endurance Thresholds:

Post Workout Combined Segments for Easy Activity Type:

| 1 | <−2% | You have significant muscle fatigue. You need to rest your legs as much as you can. Avoid hill training and speedwork for 2 days. |
|---|---|---|
| 2 | (−2% to −1%) | You have mild muscular fatigue. Don't do anything that fatigues your leg muscles! Take it easy when doing hill work and speed training in the next few workouts. |
| 3 | (−1% to 1%) | No comment. |
| 4 | >1% | Excellent, keep it up! Your legs are getting stronger! |

The post workout coaching advice for −1.4% is therefore 2 (see table above) which is: "You have mild muscular fatigue. Don't do anything that fatigues your leg muscles! Take it easy when doing hill work and speed training in the next few workouts."

Real Time Individual Segment for Easy Activity Type:

Real time performance is not provided because it is difficult to provide segment by segment performance measures.

Scoring Interpreted Data:

| <−3% | (−3% to −2%) | (−2% to −1.4%) | (−1.4% to −0.5%) | (−0.5% to 0.2%) | 0.2% to 1.4% | 1.4 to 2.3% | 2.3% to 3.4% | 3.4%-5% | >5% |
|---|---|---|---|---|---|---|---|---|---|
| 1 | 2 | 3 | 4 | 5 (=>, <) | 7 | 8 | 9 | 10 | 10 |

We will only score the combined Easy analysis. The post workout score is score for −1.4% is 4. (see table above)

Timing of 'Coaching Advice'—Real Time or Post Workout:

Post workout commentary is provided for the Easy Activity Type.

6.4 Total Performance Score:
The sum of the Performance scores will then be averaged:

|  | Endurance | Strength Endurance | Speed | Overall Performance Score |
|---|---|---|---|---|
| Up Tempo | 6 | 4 | 8 |  |
| Hills | 3 | 2 |  |  |
| Easy | 6 | 4 |  |  |
| Average: | 5 | 3.3 | 8 | 5.4 (5 + 3.3 + 8)/3 = 5.4 |

Historic Past Scores: (average of last 4 workouts containing the Activity Type)

|  | Endurance | Strength Endurance | Speed | Overall Performance Score |
|---|---|---|---|---|
| Up Tempo | 6 | 5.5 | 7 |  |
| Hills | 4 | 4 |  |  |
| Easy | 6 | 6 |  |  |
| Average: | 5.3 | 5.2 | 7 | 5.8 (5.3 + 5.2 + 7)/3 = 5.8 |

Assessing Performance:
If the current score is at least 0.2 above but not more than 1 above the historic score: "Nice Improvement"
If the current score is more than 1 above the the historic score: "Outstanding improvement"
If the current score is more than 0.2 below but not more than 1 below the historic score: "Fatigue or drop in Performance"
If the current score is more than 1 below the historic score: "Very fatigued or big drop in Performance."
If the score is equal to or between −0.2 and 0.2 in comparison to the historic score; "Performance is the same."

4.5 Assessing Total Performance Score
Performance Comparisons for the Example Workout:

|  | Current | Historic | Comment |
|---|---|---|---|
| Overall Performance | 5.4 | 5.8 | "Fatigue or drop in Performance" |
| Speed | 8 | 7 | "Nice Improvement" |
| Strength Endurance | 3.3 | 5.2 | "Very fatigued or big drop in Performance." |
| Endurance | 5 | 5.3 | "Fatigue or drop in Performance" |

In terms of diagnosis of activity, the lowest score in the above performance analysis indicates that Strength Endurance is the weak point currently being the lowest score of the 3 main areas of assessment; Endurance, Strength Endurance and Speed.

6.5 User Workout Experience
Collection of Data:
The data collected is preferably collected on special purpose devices adapted to record heart rate, speed, steps per minute, and altitude. Devices that do not record altitude are used if they have GPS because the location can be set onto a Digital Elevation Model if accurate latitude and longitude are known.

Classification of Data:
Using the classification previously explained, all Activity Types are automatically detected within the workout allowing the user to choose when it is most effective to do a particular Activity Type. Some systems have 'Rigid schedule' workouts where the user has to follow, '4 mins of Activity Type 1, 4 mins of Activity Type 2, 8 mins of Activity Type 3 and 6 mins of Activity Type 1. The problem with this is that an Up Tempo Activity Type must be completed on the flat and in the 'rigid schedule' setting this may be scheduled just as the user is about to run up a hill meaning the Up Tempo training will be impossible to do. For such a situation, recorded and analysed data will be inaccurate and meaningless and the user experience will be frustrating.

Actual Classified Activity Types Versus the Plan:
Summation of Scores and Coaching Advice:

TABLE 1

| Activity Types & Workout Duration | Planned | Actual |
|---|---|---|
| Workout Duration: | 60 mins | 70 mins |
| Anaerobic Threshold (85-95% HRmax* on flat) | 0 | 0 |
| Up Tempo (75-85% HRmax* on flat) (18 mins) | 4 reps (of 4 mins) = 16 min | 4 reps |
| Hills (>20 vertical meters) | 3 hills (60 meters) | 2 hills (80 meters) |
| Rolling Hills (>6 vertical meters, <20 meters) | 0 | 0 |

*HRmax = maximum heart rate 6.6 Coaching Advice Based on Classification and Interpretation Here is the user experience in the scheduled 60 min training example provided, where Activity Types for Up Tempo (4 reps of 4 mins) and Hills (3 hills) were scheduled.

Real Time (within the Workout as it is be Carried Out)
The user receives the plan for today's workout before starting: "Today's workout includes:
Duration: 60 mins, 4 Up Tempo and 3 Hills. Ready to Train."
The user warmed up at Easy Activity Type for 4 mins with no comment.
The user then did an Up Tempo Activity Type repetition. The Up Tempo rep which was supposed to be a duration of 4 mins correctly took 4 mins so a real time comment was given which was: "Excellent, your rep duration was correct". At the end of the Up Tempo rep the real time commentary was "$1^{st}$ Up Tempo Completed; 4 mins." And "You are faster, nice work!"
The user then trained at Easy Activity Type again with no comment.
Next the user climbed a Hill to do one of the prescribed Hills for the workout which elicited no coaching advice. At the completion of the Hill the real time commentary was; "$1^{st}$ Hill completed, 27 meters."
More Easy Activity Type with no comment was completed after the Hill.
At 20 mins a real time Compliance count up occurred explaining "Training to complete; 3 Up Tempo and 2 Hills, Time; 20 mins."
More Easy training with no comment.
A $2^{nd}$ Up Tempo repetition was then completed which this time exceeded the correct duration of 4 mins by doing 11 mins and as soon as 4 mins was exceeded the real time comment was: "Planned Rep duration exceeded, slow down" At the end of the Up Tempo rep the real time commentary was and "$2^{nd}$ Up Tempo Completed; 11 mins." "Some fatigue detected, take it easy, don't push the Up Tempo too hard."
More Easy training with no comment.
A 3rd Up Tempo repetition was done lasting 3 mins. As the user passed the prescribed total duration of Up Tempo training and the maximum total duration exceeded threshold of 16 mins 48 secs the real time commentary was: "Total Up tempo duration exceeded." At the end of the Up Tempo rep the real time commentary was "3$^{rd}$ Up Tempo Completed; 3 mins." "Rep Duration too short" And coaching advice was given; "Some fatigue detected, take it easy, don't push the Up Tempo too hard."

More Easy training with no comment.

At 40 mins a real time Compliance count up occurred which explained "Training to complete; 2 Hills, Time; 40 mins." A scheduled 4$^{th}$ Up Tempo wasn't mentioned because the total Up Tempo duration has been exceeded.

Another hill was completed and part way though the climb when a cumulative vertical meters ascended total reached 72 meters for the Hills Activity Type the comment was; "Too much Hill work, this can overtrain you or cause injury. Discontinue Hill Training" At the completion of the hill the commentary was: "2$^{nd}$ Hill completed, 53 meters."

At 60 mins a real time Compliance count up occurred explaining "All Training Complete, Well Done!" A scheduled 3$^{rd}$ Hill wasn't mentioned because the total Hills cumulative vertical meters ascended was exceeded.

At 63 mins the real time commentary was: "Prescribed workout duration exceeded."

At 70 mins the user finished the workout and was then given a report on their workout either in an auditory, text or graphical way. "Workout Complete. Duration: 70 mins, 4 Up Tempo, 2 Hills, 80 vertical meters, average speed: 5 min 40 s/km, average heart rate: 153, distance: 12.3 km. Performance Analysis: Fatigue or drop in Performance."

6.7 Post Workout Report was:

activity. The interpretation also has the flexibility to be sensor agnostic. Interpretation is 'richer' or 'poorer' depending on the data received meaning more sensors providing more data (speed, heart rate, altitude, stride rate) means more interpretation is possible and fewer sensors (speed and DEM only) means less interpretation is possible.

7. Prescription: Automated Workout or Activity Plan Modification

An Activity Plan can be adjusted in 2 ways:
The workout can be adjusted
Or the entire plan can be adjusted.
A workout can be adjusted in 2 ways:
In real time while the user is engaged in the workout
Post workout where the next workout is set up
a. Automated Updating the Workout or Activity Plan During Workout in Real Time Dynamic updating of an Activity or Activity Plan can occur in real time where the user may be part way through a workout. In this case the workout alone is adapted modifying the user's workout to be more in line with their current physical state.

For example, the user may be showing signs of fatigue after 30 min of exercise during a workout that has been set for 60 min. The advice given to the user in real time during the workout would be; "High Levels of fatigue detected, cut your workout short, go home and rest!"

Another example might be that the user has significant muscular fatigue during a 60 min run that has 80 meters of vertical ascent or 4×20 meter hills that need to be completed.

| Workout Duration: | "Exercise Duration exceeded plan, please follow the plan carefully" |
|---|---|
| Up Tempo | |
| Compliance: | "Too much speedwork is a bad thing, apart from increasing chance of injury, it causes high fatigue, upsets your energy for other workouts and can predispose you to illness." |
| | "You need to progressively increase the number of reps of a Activity Type that you do to get an improvement. The training program will guide you on this." |
| Performance | "You have mild muscular fatigue, take it easy with the muscular aspects of the next workout" |
| | "You showed a speed increase during Up Tempo training today." |
| Hills | |
| Compliance: | "Without a steady increase in your hill work you don't get the stimulus that drives your strength endurance up. Increase the number of hills you are doing gradually each session." |
| | "Doing more climbing than is in the Activity Plan is counterproductive, you are far more likely to disrupt the balance of the program, get fatigued or worse, get injured. Follow the plan." |
| Performance: | "Slight cardiovascular fatigue, go easy in the next workout" |
| | "You have significant muscle fatigue. You need to rest your legs as much as you can. Avoid hill training and speedwork for 2 days." |
| Easy | |
| Performance | "You have significant muscle fatigue. You need to rest your legs as much as you can. Avoid hill training and speedwork for 2 days." |
| Workout Performance Analysis: | |
| Endurance | "Fatigue or drop in Performance" |
| Strength Endurance | "Very fatigued or big drop in Performance." |
| Speed | "Nice Improvement" |
| Overall Performance | "Fatigue or drop in Performance" |

Interpretation System Flexibility; Multi Sport and Multi Sensor

While the above commentary example applies to a sports performance situation the system can be equally used for recreational exercise, weight loss and many other forms of Muscular fatigue in this case means tired legs and so while the user might be comfortable and get improvements out of doing 60 mins of easy running, it is probably unwise to do the hill training today because of the leg fatigue. In this case the advice would be: "Significant leg fatigue detected, continue the workout but delete all hill training today!"

b. Updating and Altering the Plan:

The updating of the plan involves 3 forms of alteration to the plan:
- the altering the occurrence of Activity Types,
- altering the volume or number of the Activity Types
- or altering the overall volume (duration or distance) of the workout.

Altering the Activity Types means reducing, increasing or eliminating some Activity Types, in some cases in favour of others.

Altering the Activity Type volumes means increasing or decreasing the duration, distance or number of segments/repetitions of a particular Activity Type.

Altering the overall volume means increasing or decreasing the duration or distance (in some cases the repetitions) of a workout or series of workouts.

All of this means that different Activity Types are emphasized or diminished. This effects what the user's body is adapting to, changing the 'mix' of physiological effects on the users trained abilities. This is rather like changing the 'recipe' for a cake in that if the ingredients, quantities of ingredients or how long the cake is baked for, are changed, they can create remarkably different outcomes. In this case it is related to the user's physiological improvements and new 'trained' physical attributes.

7.1 Real Time Workout Modification

In order to show a real time workout adjustment we need to show the plan for a workout, the training that has been completed (current) and the remaining training (remaining) to be completed in the workout. (see FIG. 3 below)

For the purposes we will use the following workout plan:

TABLE 2

| Activity Type/Total Workout Volume | Planned | Current* | Remaining** |
|---|---|---|---|
| Total Duration | 40 mins | 13 min | 27 min(40-13) |
| Anaerobic Threshold | 2 (×3 mins) | 1 (×3 mins) | 1 (×3 mins) |
| Up Tempo | 5 (×4 mins) | 1 (×4 mins) | 4 (×4 min) |
| Hills | 4 hill | 1 hill | 3 hills |
| Rolling Hills | 5 rolling hills | 1 rolling hill | 4 rolling hills |
| Easy | (no plan, Easy occurs, when other Activity Types are not used) | | |

*Current means the training that has been completed up to a point in time, part way through the workout and workout plan.
**Remaining means the elements of the plan that have not been completed.

a. Real Time Total Training Volume Adjustment

Real Time Total Training Volume adjustments occur during the workout. Assessments are made after the first 33% of the workout and after 66% of the workout.

Therefore for a 40 min workout (see FIG. 3), assessments are made at 33% of 40 mins which is the 13 min mark and at 66% of 40 mins which is the 26 min mark.

If the user were exercising in a 40 min workout, an assessment of the users Easy Activity Type's Endurance performance data is made at the 33% and 66% marks of the total workout duration. So for example, at the 13 min mark an assessment is made of the users Easy Activity Type Endurance up to that point in the workout.

Easy Activity Type Endurance is assessed in real time as the user works through the session where the Endurance value is compared to the historic Endurance measure for Easy Activity Type.

The value at the 33% mark during today's workout is 3% less than the historic value. This is then applied to the following table:

| 1 | >3% | Add 20 mins (on selected workouts) |
|---|---|---|
| 2 | 2% to 3% | Add 10 mins (on selected workouts) |
| 3 | 1% to 2% | Add 5 mins (on selected workouts) |
| 4 | 1% to -1% | No Change, continue workout |
| 5 | (-1% to -2%) | Shorten workout duration by 10% |
| 6 | (-2% to -3%) | Shorten workout duration by 20% |
| 7 | (-3% to -4%) | Shorten workout duration by 50% |
| 8 | >-4% | Cancel Workout |

The correct modification to apply to the workout plan is 6 (in the table above) which is to shorten the workout by 20%. 20% of 40 mins is 8 mins so the new workout duration is calculated at 32 mins.

A short comment is supplied for 6 (in the table above) at the 33% mark through the workout informing the user during their workout that the workout has been shortened:

"Cardiovascular Fatigue Detected so the Workout has been Shortened to 32 Mins."

| 1 | >3% | You are fitter today so I am extending the workout by 20 mins maing the total workout X. |
|---|---|---|
| 2 | 2% to 3% | There is an increase in fitness today so the workout will be increased by 10 mins making the total duration |
| 3 | 1% to 2% | Slight fitness increase so 5 mins extra has been added to todays workout. |
| 4 | 1% to -1% | no comment |
| 5 | (-1% to -2%) | Slight cardivacular fatigue detected, the workout is being shortened to X |
| 6 | (-2% to -3%) | Cardiovascular fatigue has been detected so the workout has now been shortened to X. |
| 7 | (-3% to -4%) | High Cardiovascular fatigue, your workout has been adjusted and significantly shortened to X. |
| 8 | >-4% | Significant cardiovascular fatigue detected, the workout is canceled. Stop the workout. X is the calculated new workout total volume (e.g. 100 mins shortened by 50% is 50 mins) |

In the second assessment when the user is 66% of the way through the workout the changes do not contribute to changes that have already been made For example a high fitness level might mean adding 20 min to the workout at the 33% mark. At the 66% mark this figure is either confirmed or adjusted but another 20 mins is not added to the workout.

Muscle Endurance Activity Type Adjustments

Muscle endurance training involves training the muscle endurance by applying load. The Activity Types that do this are: Rolling Hills and Hills.

In the same way as the total workout volume assessment, an analysis occurs at the 33% and 66% mark during the workout as the user is carrying out the activity session.

The plan for Rolling Hills is to do 5 Rolling Hills and the plan for Hills is to do 4 Hills. In the workout so far, the user has completed 1 Rolling Hill and 1 Hill so there is still 4 Rolling Hills and 3 Hills scheduled to be completed within the workout in the remaining time. (see FIG. 3) An assessment is made of the users Strength Endurance in the workout for Rolling Hills and Hills.

b. Rolling Hills Assessment

In FIG. 3, the user is 33% of the way through their workout and 1 Rolling Hill has been completed in the workout so far. There are 4 Rolling Hills remaining to be done that are scheduled.

The first Rolling Hills shows a 2.8% drop (-2.8%) in Strength Endurance versus the historic value.

This −2.8% drop is then applied to the following table:

| 1 | >2% | Increase reps by 30% |
|---|---|---|
| 2 | 1% to 2% | Increase reps by 15% |
| 3 | 1% to −1% | No Change, continue workout |
| 4 | (−1% to −2%) | Reduce reps by 30% |
| 5 | (−2% to −3%) | Reduce reps by 50% |
| 6 | (−3% to −4%) | Reduce reps by 80% |
| 7 | >−4% | Cancel Training Type |

The correct plan modification is 5 (see table above) which requires that the remaining number of scheduled Rolling Hills for the workout should be reduced by 50%.

There are 4 remaining Rolling Hills within the workout and these need to be reduced by 50% meaning that the new remaining number of scheduled Rolling Hills scheduled to be completed in the workout is now 2 Rolling Hills.

A short comment is supplied for 5 (see table above) at the 33% mark through workout informing the user during the planned amount for Rolling Hills to be completed within the workout has been reduced: "Moderate muscular fatigue has been detected, the remaining number if rolling hills to be completed has been reduced to 2 rolling hills."

| 1 | >2% | Your strength endurance has increased, we will increase the remaining number of rolling hills to be completed. |
|---|---|---|
| 2 | 1% to 2% | There is a slight strength endurance improvement so we will increase the remaining number of rolling hills |
| 3 | 1% to −1% | no comment |
| 4 | (−1% to −2%) | Mild muscular fatigue is detected, I will slightly reduce the remaining number of rolling hills to be completed to X. |
| 5 | (−2% to −3%) | Moderate muscular fatigue has been detected, the remaining number of rolling hills to be completed has been reduced to X. |
| 6 | (−3% to −4%) | High muscular fatigue identified, I have significantly reduced the remaining rolling hills to be completed to X. |
| 7 | >−4% | Significant muscular fatigue, all rolling hills training is canceled for this workout. X is the calculated new rolling hills volume. (e.g. 4 rolling hills reduced by 50% is 2 rolling hills) |

In the second assessment when the user is 66% of the way through the workout the changes do not contribute to changes that have already been made if the adjustment is for an increase. If training is being decreased, the second assessment can contribute to the first where the first assessment may reduce training by 50% and then the second assessment might cancel the workout. For example a high strength endurance level might mean adding 2 extra rolling hills to the workout at the 33% mark. At the 66% mark this figure is either confirmed or adjusted but another 2 extra rolling hills is not added to the workout.

c. Hills Assessment

The user is 33% of the way through their workout and 1 Hill has been completed so far. There are 3 Hills remaining to be done that are planned for the present workout. (see FIG. 3) The first Hill shows a 1.3% drop (−1.3%) in Strength Endurance versus the historic value. This −1.3% drop is then applied to the following table:

| 1 | >2% | Increase reps by 30% |
|---|---|---|
| 2 | 1% to 2% | Increase reps by 15% |
| 3 | 1% to −1% | No Change, continue workout |
| 4 | (−1% to −2%) | Reduce reps by 30% |
| 5 | (−2% to −3%) | Reduce reps by 50% |
| 6 | (−3% to −4%) | Reduce reps by 80% |
| 7 | >−4% | Cancel Training Type |

The correct prescription is 4 (see the table above) which requires that the remaining number of scheduled hills for the workout should be reduced by 30%.

There are 3 remaining hills within the workout and these need to be reduced by 30% meaning that the new remaining number of scheduled hills scheduled to be completed in the workout is now 2 hills (when rounded to the nearest whole number).

2 hills are now scheduled to be completed during the remaining duration of the workout as opposed to the original plan of 3 remaining hills needing to be completed.

A short comment is supplied for 5 (see table below) at the 33% mark through workout informing the user that the planned amount for Hills to be completed within the workout has been reduced: "Mild muscular fatigue detected, I will slightly reduce the remaining number of hills to be completed in the workout to 2 hills."

| 1 | >2% | Your strength endurance has increased, we will increase the remaining number of hills to be completed in |
|---|---|---|
| 2 | 1% to 2% | There is a slight strength endurance improvement so we will increase the remaining number of hills to be |
| 3 | 1% to −1% | no comment |
| 4 | (−1% to −2%) | Mild muscular fatigue is detected, I will slightly reduce the remaining number of hills to be completed in the |
| 5 | (−2% to −3%) | Moderate muscular fatigue has been detected, the remaining number of hills to be completed has been re |
| 6 | (−3% to −4%) | High muscular fatigue identified, I have significantly reduced the remaining hills to be completed to X. |
| 7 | >−4% | Significant muscular fatigue, all hills training is canceled for this workout. X is the calculated new hills volume. (e.g. 4 hills reduced by 50% is 2 hills) |

In the second assessment when the user is 66% of the way through the workout the changes do not contribute to changes that have already been made if the adjustment is for an increase. If training is being decreased, the second assessment can contribute to the first where the first assessment may reduce training by 50% and then the second assessment might cancel the workout. For example a high strength endurance level might mean adding 2 extra hills to the workout at the 33% mark. At the 66% mark this figure is either confirmed or adjusted but another 2 extra hills is not added to the workout.

Speed Activity Type Adjustments

Speed training involves training the user's speed ability. The Activity Types that do this are: Up Tempo and Anaerobic Threshold.

In the same way as the total workout volume assessment and the muscle endurance Activity Type assessments, an analysis occurs at the 33% and 66% mark during the workout as the user is carrying out the activity session.

The plan (see FIG. 3) for the Up Tempo Activity Type is to do 5 repetitions of 4 mins each and the plan for the Anaerobic Threshold Activity Type is to do 2 repetitions of 3 mins each. So far in the workout the user has completed 1 Up Tempo repetition and 1 Anaerobic Threshold repetition so there is still 4 repetitions of Up Tempo and 1 repetition of Anaerobic Threshold scheduled to be completed within the workout in the remaining time. (see FIG. 3) An assessment is made of the users speed in the workout by averaging the data within each Activity Type classification of Up Tempo and Anaerobic Threshold. This assessment is carried out at the 33% and 66% marks during the workout duration meaning all speed workout data for Up Tempo and Anaerobic Threshold is analysed up to that point.

In this case 1 repetition of Up Tempo has been completed and 1 repetition of Anaerobic Threshold has been completed by the 33% mark so assessments can be made on adjusting both the Up Tempo and Anaerobic Threshold repetition plans for the workout. If an Activity Type has not been completed by the 33% or 66% mark of total workout duration, the assessment of the Activity Type cannot take place. If the Activity Type reps are completed then no additions occur.

d. Up Tempo Assessment

The user is 33% of the way through their workout and 1 Up Tempo repetition has been completed in the workout so far. There are 4 Up Tempo repetitions remaining to be done that are planned for the present workout.

The Up Tempo training so far shows a 1.9% increase in Speed versus the historic value. This 1.9% increase is then applied to the following table:

| 1 | >2% | Increase reps by 30% |
|---|---|---|
| 2 | 1% to 2% | Increase reps by 15% |
| 3 | 1% to −1% | No Change, continue workout |
| 4 | (−1% to −2%) | Reduce reps by 30% |
| 5 | (−2% to −3%) | Reduce reps by 50% |
| 6 | (−3% to −4%) | Reduce reps by 80% |
| 7 | >−4% | Cancel Training Type |

The correct prescription is 2 (see table above) which requires that the remaining number of scheduled Up Tempo repetitions for the workout should be increased by 15%.

There are 4 remaining Up Tempo repetitions within the workout and these need to be increased by 15%. 15% of 4 is 0.6 and when rounded to the nearest whole number means adding 1 extra Up Tempo repetition. Had the remaining number been 3 Up Tempo repetitions then 15% of 3 would be 0.45 which when rounded to the nearest whole number would be 0 so no extra repetitions would be added. In this case the new remaining number of Up Tempo scheduled to be completed in the workout is now 5 Up Tempo repetitions.

5 Up Tempo Repetitions are now scheduled to be completed during the remaining duration of the workout.

A short comment is supplied for 2 at the 33% mark through workout informing the user during their exercise that the planned amount for Up Tempo to be completed within the workout has been increased: "You have had an improvement in your speed so I will increase your Up tempo reps today slightly to 5 reps."

| 1 | >2% | Your speed is increased significantly, I will increase the remaining Up Tempo reps to X. |
|---|---|---|
| 2 | 1% to 2% | You have had an improvement in your speed so I will increase your Up tempo reps for today slightly to X. |
| 3 | 1% to −1% | no comment |
| 4 | (−1% to −2%) | Mild fatigue detected, I will reduce your Up Tempo reps for today to X. |
| 5 | (−2% to −3%) | Moderate faitugue identified, your remining Up Tempo reps will be reduced to X. |
| 6 | (−3% to −4%) | High fatigue detected, I will significantly reduce your remaining Up Tempo reps for todays workout to X. |
| 7 | >−4% | Severe fatigue, all Up tempo is cancelld for this workout. X is the calculated new Up Tempo Reps (e.g. 4 up tempo reps reduced by 50% is 2 up tempo reps) |

In the second assessment when the user is 66% of the way through the workout the changes do not contribute to changes that have already been made if the adjustment is for an increase. If training is being decreased, the second assessment can contribute to the first where the first assessment may reduce training by 50% and then the second assessment might cancel the workout. For example a high speed result might mean adding 2 extra Up Tempo repetitions to the workout at the 33% mark. At the 66% mark this figure is either confirmed or adjusted but another 2 extra Up Tempo repetitions is not added to the workout.

e. Anaerobic Threshold Assessment

The user is 33% of the way through their workout and 1 Anaerobic Threshold repetition has been completed in the workout so far. There is 1 Anaerobic Threshold repetition remaining to be done that is planned for the present workout.

The Anaerobic Threshold repetition shows a 4.5% drop in strength endurance versus the historic value.

This 4.5% (−4.5%) drop is then applied to the following table:

| 1 | >2% | Increase reps by 30% |
|---|---|---|
| 2 | 1% to 2% | Increase reps by 15% |
| 3 | 1% to −1% | No Change, continue workout |
| 4 | (−1% to −2%) | Reduce reps by 30% |
| 5 | (−2% to −3%) | Reduce reps by 50% |
| 6 | (−3% to −4%) | Reduce reps by 80% |
| 7 | >−4% | Cancel Training Type |

The correct prescription is 7 (see table above) which requires that the remaining number of scheduled Anaerobic Threshold repetitions for the workout be cancelled.

There is 1 remaining Anaerobic Threshold repetition within the workout and this will be cancelled meaning that the new remaining number of Anaerobic Threshold repetitions scheduled to be completed in the workout is now 0.

No Anaerobic Threshold is now scheduled to be completed during the remaining duration of the workout as opposed to the original plan of 1 remaining Anaerobic Threshold repetition needing to be completed.

A short comment is supplied for 7 (see the table below) at the 33% mark through workout informing the user during their exercise that the planned amount for Anaerobic threshold to be completed within the workout has been cancelled: "Severe fatigue, all Anaerobic threshold is cancelled for this workout."

| 1 | >2% | Your speed is increased significantly, I will increase the remaining Anaerobic Threshold reps to X. |
|---|---|---|
| 2 | 1% to 2% | You have had an improvement in your speed so I will increase your Anaerobic Threshold reps for today slightly to X. |
| 3 | 1% to −1% | No comment. |
| 4 | (−1% to −2%) | Mild fatigue detected, I will reduce your Anaerobic Threshold reps for today to X. |
| 5 | (−2% to −3%) | Moderate faitugue identified, your remaining Anaerobic Threshold reps will be reduced to X. |

| | | |
|---|---|---|
| 6 | (−3% to −4%) | High fatigue detected, I will significantly reduce your remaining Anaerobic Threshold reps for todays workout to X. |
| 7 | >−4% | Severe fatigue, all Anaerobic Threshold is cancelld for this workout. X is the calculated new Anaerobic Threshold Reps (e.g. 4 Anaerobic Threshold reps reduced by 50% is 2 |

In the second assessment when the user is 66% of the way through the workout the changes if required do not contribute to changes that have already been made if the adjustment is for an increase. If training is being decreased, the second assessment can contribute to the first where the first assessment may reduce training by 50% and then the second assessment might cancel the workout. For example a high strength endurance level might mean adding 2 extra Anaerobic Threshold repetitions to the workout at the 33% mark. At the 66% mark this figure is either confirmed or adjusted but another 2 extra Anaerobic Threshold repetitions is not added to the workout.

f. Summary of Current Real Time Workout Adjustment:

Current values 33% of the way through a 40 min workout currently at the 13 min mark:

TABLE 3

Activity Type/Total Workout Volume

| | Planned Remaining** | Current | Old Remaining* | New |
|---|---|---|---|---|
| Total Duration | 40 mins | 13 min | 27 min (40 − 13) | 19 min (32 − 13) |
| Anaerobic Threshold | 2 (x3 mins) | 1 (x3 mins) | 1 (x3 mins) | 0 |
| Up Tempo | 5 (x4 mins) | 1 (x4 mins) | 4 (x4 min) | 5 (x4 min) |
| Hills | 4 Hill | 1 Hill | 3 Hills | 2 Hills |
| Rolling Hills | 5 Rolling Hills | 1 Rolling Hill | 4 Rolling Hills | 2 Rolling Hills |
| Easy | (no plan, Easy occurs, when other Activity Types are not used) | | | |

*Old Remaining is the elements of the Activity Plan left to be completed within the workout
**New Remaining means the elements of the Activity Plan left to be completed within the workout once the real time workout adjustments have taken place.

g. Prescription Commentary at 13 Min (33%) Mark in the 40 Min Workout:

| | |
|---|---|
| Workout | "Cardiovascular fatigue detected so the workout has been shortened to 32 mins." |
| Rolling Hills | "Moderate muscular fatigue has been detected, the remaining number if rolling hills to be completed has been reduced to 2 rolling hills." |
| Hills | "Mild muscular fatigue detected, I will slightly reduce the remaining number of hills to be completed in the workout to 2 hills." |
| Up Tempo | "You have had an improvement in your speed so I will increase your Up tempo reps today slightly to 5 reps." |
| Anaerobic Threshold | "Severe fatigue, all Anaerobic threshold is cancelled for this workout." | h. Post Workout Adjustment where the Next Workout is Set Up

A similar system to the above can determine adjustments in following workouts using the data obtained in the assessment at the end of the currently completed workout.

The values obtained for the currently completed workout are:

| | |
|---|---|
| Training Volume adjustment | shorten workout by 20% |

Speed Training Adjustments

| | |
|---|---|
| Anaerobic threshold adjustments | cancel all anaerobic threshold training |
| Up tempo adjustments | increase by 15% |

Muscle endurance Activity Type adjustments

| | |
|---|---|
| Hills adjustment | reduce Hills reps by 30% |
| Rolling Hills adjustments | reduce Rolling Hills reps by 50% |

These adjustments can then be applied to the next workout to be completed the following day. The most recent end of workout analysis defines the changes to the following workout. If there is a gap of more than 2 days the workout reverts back to what was in the original plan.

The following 2 examples show adjustments based on the users physical state in the current workout that can be applied to the next prescribed workout in the long term Activity Plan to optimise their training.

TABLE 4

| Activity Type & Workout Duration | Planned Workout | Adjustment | Adjusted Workout |
|---|---|---|---|
| Training Volume Duration: | 80 mins | −20% | 64 mns |
| Anaerobic Threshold | 0 | delete | 0 |
| Up tempo | 0 | +15% | 0 |
| Hills | 2 Hills | −30% | 1 Hill* |
| Rolling Hills (the remaining exercise is Easy) | 8 Rolling Hills | −50% | 4 Rolling Hills |

*30% of 2 is 0.6 which means 1.4 Hills, when rounded to the nearest whole number the value is 1.

TABLE 5

| Activity Type & Workout Duration | Planned Workout | Adjustment | Adjusted Workout |
|---|---|---|---|
| Training Volume Duration: | 40 mins | −20% | 32 mns |
| Anaerobic Threshold | 2 (x3 mins) | delete | 0 |
| Up tempo | 4 (x6 mins) | +15% | 5 (x6 mins)* |
| Hills | 0 | −30% | 1 Hill** |
| Rolling Hills | 2 Rolling Hills | −50% | 4 Rolling Hills*** |

TABLE 5-continued

| Activity Type & Workout Duration | Planned Workout | Adjustment | Adjusted Workout |
|---|---|---|---|
| (the remaining exercise is Easy) | | | 5 |

*15% of 4 is 0.6 so +15% is 4.6 when rounded to the nearest whole number is 5.
**−30% of 0 is 0
***−50% of 2 is 1 which means 1 Hill 7.2-Activity Plan Modification Linking and Progression of Activity Types Over Time within an Activity Plan Each Activity Type is linked within an activity plan to create a progression. In sequence Activity Types are introduced, emphasized and maintained in a progression of changing volumes (and in some cases intensity) over time. This is because the body gradually adapts to changing workloads. Too much change leads to injury and illness, too little change means that there is nothing for the body to adapt to, which means no physiological improvements, so there must be a progressive change in Activity Types. This is referred to as 'progressive overload'.

Linking and Progression can be Shown as Follows in a Sample Long Term Activity Plan Example:

TABLE 6

| Activity Type | Wk 1 | Wk 2 | Wk 3 | Wk 4 | Wk 5 | Wk 6 | Wk 7 | Wk 8 | Wk 9 | Wk 10 |
|---|---|---|---|---|---|---|---|---|---|---|
| Hills (vertical meters) | 20 | 40 | 60 | 80 | 100 | 120 | 140 | 160 | 180 | 200 |
| Up Tempo (mins) | 0 | 0 | 0 | 4 | 6 | 8 | 10 | 12 | 14 | 16 |

The above example shows a gradual progression of 2 Activity Types in terms of volume. They are linked in that to change one week's Activity Type value means that to maintain the gradual progression, all the other volumes for the Activity Type need to be adapted simultaneously.

Obviously perfect compliance to the plan is rare so the plan needs to be automatically adjusted on a regular basis to keep in line with the users actions. If training is missed or a workout needs to be adjusted based on the user's physiology then the whole plan must be adapted because of the linked progressions of Activity Types.

a. Automatically Updating a Workout in Real Time or Across the Entire Activity Plan Automated Updating of the Entire Activity Plan The entire Activity Plan may be altered where scheduled training that is missed or not fully completed will affect the progression of the volumes for that Activity Type for the rest of the training program. Also, the system may identify a weakness and modify the volumes of one or more Activity Types by emphasizing one Activity Type like Up Tempo and reducing another Activity Type like Rolling Hills-effecting the linked progressions in volume for both Activity Types through the remaining Activity Plan or training program.

b. Altering a Single Activity Type Progression

For example if the 20 vertical meters ascended scheduled for week 1 of the Activity Plan was missed, the user would now have to do 100% more (i.e. start at 40 vertical meters) in week 2 leading to possible injury. (see table below)

TABLE 7

Total Weekly Training Volumes for Activity TypeActivity Types

| Activity Type | Current week Wk 1 | Wk 2 | Wk 3 | Wk 4 | Wk 5 | Wk 6 | Wk 7 | Wk 8 | Wk 9 | Wk 10 |
|---|---|---|---|---|---|---|---|---|---|---|
| Hills (vertical meters) | 20 | 40 | 60 | 80 | 100 | 120 | 140 | 160 | 180 | 200 |
| Up Tempo (mins) | 0 | 0 | 0 | 4 | 6 | 8 | 10 | 12 | 14 | 16 |

The Activity Plan must therefore be able to automatically update in response to the data received which in this case would be that the Hill training had not been completed in week 1. The system (see table below) would update by starting the Hills Activity Type Progression one week later to keep the progression the same and would remove the maximum week (week 10, 200 in the above table).

TABLE 8

This automated update may follow:

| Activity Type | Wk 1 | Wk 2 | Wk 3 | Wk 4 | Wk 5 | Wk 6 | Wk 7 | Wk 8 | Wk 9 | Wk 10 |
|---|---|---|---|---|---|---|---|---|---|---|
| Hills (vertical meters) | 0 | 20 | 40 | 60 | 80 | 100 | 120 | 140 | 160 | 180 |
| Up Tempo (mins) | 0 | 0 | 0 | 4 | 6 | 8 | 10 | 12 | 14 | 16 |

To demonstrate another example, in week 6 the User may not have completed enough duration in the Up Tempo Activity Type which may have only been 2 mins instead of the 8 mins scheduled (see table above).

The system in this cases chooses a value half way between what was done and the original plan and continues to do this over the following weeks till the progression is back on plan. (see table below compared to table above)

The automated alteration of the Activity Plan might include a slight adjustment:

TABLE 9

| Activity Type | Wk 1 | Wk 2 | Wk 3 | Wk 4 | Wk 5 | Current week Wk 6 | Wk 7 | Wk 8 | Wk 9 | Wk 10 |
|---|---|---|---|---|---|---|---|---|---|---|
| Hills (vertical meters) | 20 | 40 | 60 | 80 | 100 | 120 | 140 | 160 | 180 | 200 |
| Up Tempo (mins) | 0 | 0 | 0 | 4 | 6 | 2* | 6** | 9*** | 12**** | 14 |

*Incomplete training (2 completed instead of 8 repetitions)
**Original plan = 10, Wks Previous reps = 2, 10 − 2 = 8. Half way between is 8 ÷ 2 = 4.4 + 2 = 6
***Original plan = 12, Wks Previous reps = 6, 12 − 6 = 6. Half way between is 6 ÷ 2 = 3.3 + 6 = 9
****Original plan = 14, Wks Previous reps = 9, 14 − 9 = 5. Half way between is 5 ÷ 2 = 2.5. 2.5 + 9 = 12 (rounded)

In another example, the user may have done too much Up Tempo in week 6 where they had 8 mins prescribed and did 12 mins. The fatigue and improvement measures show that the user was able to cope with the increase and the alteration would be to increase the amount of Up Tempo by continuing the same percentage progression already used in the plan but using the new higher rep or volume number.

TABLE 10

| Activity Type | Wk 1 | Wk 2 | Wk 3 | Wk 4 | Wk 5 | Current week Wk 6 | Wk 7 | Wk 8 | Wk 9 | Wk 10 |
|---|---|---|---|---|---|---|---|---|---|---|
| Hills (vertical meters) | 20 | 40 | 60 | 80 | 100 | 120 | 140 | 160 | 180 | 200 |
| Up Tempo (mins) | 0 | 0 | 0 | 4 | 6 | 12 | 14 | 16 | 18 | 20 | c. Altering Multiple Activity Type Progressions

In some cases measurement of strength endurance levels and speed may show that the user has a specific need to develop a specific area of their physiology due to the fact that it is weak or another area is very well developed.

In this example, Strength Endurance is trained by the Activity Type Hills. To get a strength improvement the user needs to do Hill training. Speed is characterized by the Up Tempo Activity Type and improvements in speed would require training at Up Tempo. During the Users training, a strong Speed ability is detected but a poor Strength Endurance is also ascertained. This requires that Speed training be diminished and Strength Endurance training be emphasized. This would mean that the system would reduce the Up Tempo training within the Activity Plan and increase the Hills training like this:

TABLE 11

| Activity Type | Wk 1 | Wk 2 | Wk 3 | Wk 4 | Wk 5 | Wk 6 | Wk 7 | Wk 8 | Wk 9 | Wk 10 |
|---|---|---|---|---|---|---|---|---|---|---|
| Hills (vertical meters) | 20 | 40 | 65 | 85 | 110 | 135 | 165 | 195 | 215 | 245 |
| Up Tempo (mins) | 0 | 0 | 0 | 0 | 0 | 4 | 8 | 12 | 14 | 16 |

In this way the system is constantly updating the activity plan to closely fit with the users current needs.

8. Definitions of Sensor Types

The system is able to be configured to many different types of sensors and therefore is not bound to a specific device but rather may use many different types of special purpose devices so long as they contain the required sensors and provide the right parameters. It may occur also that the system utilizes data from sensors from several different devices as is the case with using a smart phone with internal GPS and heart rate data from a Zephyr HRM BT or the barometric, temperature, GPS and heart rate data from a FRWD B series device combined with the internal accelerometer found in a smart phone.

Each specialist activity sensing category: Activity Status Monitoring, Weight Loss and Walking, Running, Cycling, Rowing and Kayaking, Horse Training and Pedometer Monitoring will now be covered in terms of sensors required and current devices that are available in the market that could utilize the system of the invention. The following exemplary devices are not intended to limit the scope of the invention and other devices capable of providing the correct measurements for the system algorithms may be used instead and as required by the particular application.

8.1 Activity Status Monitoring: (Health, Military, Fire and Rescue Services)

For all Activity Monitoring Classifications the sensor requirements are the same. They all require some measure of altitude change combined with an intensity measure which can include measurements of speed, power or heart rate. Biomedical parameters such as ECG, blood pressure and Heart Rate Variability may also be used.

Altitude Change:

Altitude change can be measured in many different ways through special purpose sensor devices. These include barometers, inclinometers, Digital Elevation Models and GPS. Altitude change is a way in which a sensor can determine the terrain the user is on. For example an increase in altitude or gradient indicates that the user is moving uphill, a decrease in vertical meters or a decline means the user is going downhill and no altitude change or a flat gradient or slope means the user is on the flat.

Many devices currently contain digital barometers and thermometers. Examples include Suunto sports watches (e.g. Suunto X6 & T6), the Timex Altitude Barometer Adventure Tech watch, the Casio Pathfinder series of watches and Polar Heart Rate devices (e.g. RS800, CS600 etc).

There are also handheld barometers such as the Nova Lnyx 230-M202 and VWR handheld digital barometer 4198, both of which use barometric pressure to measure altitude.

Suunto and some cycle computer companies include inclinometers on their devices to measure slope/gradient change.

A digital elevation model (DEM) is a digital representation of ground surface topography or terrain. Various data sets are available of differing accuracy levels based on satellite surveys of the earth including the Shuttle Radar Topography mission in 2000. Once the coordinates of a user are known their position can be overlaid onto the topography of their location in real time or in post processing. Digital Elevation Models (sometimes known as Digital Terrain Models) are used for post processing of data by companies like Bones in Motion and Sportsdo.

Garmin uses GPS in its Forerunner 205, 305 and 405 series watches to show altitude. Garmin also have devices like the Garmin eTrex Summit HC which are handheld and contain a barometer for altitude. GPS altitude is obtained by the triangulation of satellites in the sky overhead at the time.

Intensity:

Speed

Speed can be measured a number of ways through a number of sensors from crude accelerometer algorithms like in the Zephyr HRM BT, Nike+ and the Timex Pedometer with Speed, through to more sophisticated algorithms like Dynastream use in their speed pods which are licensed to companies like Polar for their RS800, FT80 and 625 products, and like the Adidas micoach Pacer and Suunto T6.

Other devices such as Fitbit, Fitlinxx Actiped and Directlife track activity through accelerometers. Bodymedia's Fit system, Mytrak's M2 and Polar's FA20 all track movement but not necessarily speed.

GPS can also be used to obtain speed data and is used in a host of devices such as the Polar G3 GPS sensor, the Garmin Forerunner 205, 305 and 405 models as well as many apps like Runkeeper, Sportsdo and Bones in Motion X app that rely on either mobile phones with internal GPS or linked to an external GPS.

There are devices like the Mobimotion Spurty chest strap that contains both a heart rate monitor and GPS that Bluetooth data to a phone and many other devices that accept and log Bluetooth data such as the FRWD W and B series.

In the case of military, fire and rescue services, the system could switch from outdoor location to indoor location detection. Crude speed measures could utilise infrared, ultrasonic, RFID, UWB and signal strength systems.

Power

Power for a walker or runner currently can only be inferred by applying a Power algorithm to the data based on speed, the user's weight and the slope or gradient at the time.

It may not be too long before power will be more directly measured using force plates in shoes or by converting acceleration data in a shoe to power.

Crude power measures may be able to be inferred from the above mentioned indoor location detection systems.

Heart Rate

Heart rate can be measured directly currently through a strap that contains 2 electrodes that is placed across the chest and was originally designed by Polar Electro which filed its patent in 1979 and is the world leader in wireless chest strap heart rate monitors. The patent has now expired and many other companies use this technology including Timex, Suunto, Garmin, Cardiosport, Impulse and Zephyr.

There are now many Heart Rate Monitor straps like the Zephyr HRM BT and the Mobimotion Spurty chest strap that do not have a data receiver but rather Bluetooth data to devices like a mobile phone. Still other devices like the SMHeartLink act as a bluetooth receiver for the Apple iphone to accept heart rate data from a heart rate strap and the FRWD B series devices that are able to receive broadcast heart rate data from most wireless heart rate straps and resend the data to a phone via BluetoothOther devices receive broadcast data using the ANT+ signal.

There are other methods to obtain heart rate which includes a strapless heart monitor like the Mio heart rate monitor that requires the user to place 2 fingers on the electrodes on the watch face to obtain heart rate measurement.

It is possible to obtain heart rate through infrared where light change is used to measure heart beats and also disposable electrodes as opposed to straps.

R-R (Relaxation Rate) or HRV (Heart Rate Variability) could also be used to measure intensity on the body. Heart rate variability measures the average of the time (in ms) between a series of heart beats and the more intense the effort the more uniform the time between heart beats. FRWD, and some Suunto and Polar devices are able to measure heart rate variability. It is conceivable that in the very near future heart rate may be able to be measured through the wrist, finger or via some other means which may include Respiration Rate. Respiration rate is calculated by measuring expansion of the chest using a chest strap as used in the Zephyr Bioharness. Another method for measuring heart rate as in the Firstbeat licensed system to Suunto and FRWD derives respiration rate and ventilation (which could also be used to measure intensity) through heart rate which increases during inhalation.

Stride Rate

Stride rate may also be used as an extra classification parameter. This involves the use of an accelerometer that records the repetitive impact for each stride which is then summed over 1 minute of time providing a measure of strides per minute. Stride rate is a handy extra measure as it can be used to determine the speed of leg movement which further contributes to building a picture of what the user is doing. A stride rate of 55 strides per minute indicates that the user is walking, 80 strides per minute is easy running, and 90 strides per minute would be fast running for example. The Polar RS800 measures and displays stride rate in real time and most smart phones contain accelerometers these days which can be used to measure stride rates on a phone by counting impacts over time.

There are 3 inactive classifications within Activity Status Monitoring; Inactive Upright, Inactive Rest and Inactive Prone. None of these use altitude change to classify the activity. But rather use speed, heart rate (or respiration rate) and an accelerometer.

Positional Status (Accelerometer)

All Inactive classifications require a positional status measurement via an accelerometer as seen in most smart phones these days which use 2 or 3 axis sensors within the accelerometer to determine whether the device is upright or prone which can in turn determine whether the user (or device at least) is vertical or horizontal so long as the device is in a fixed position on the user.

Movement (Speed)

Speed can be established using an accelerometer or GPS to determine whether the user is moving or stationary. Power can be inferred from speed.

8.2 Weight Loss—Walking and Running Classification

All weight loss classifications use exactly the same sensor measurement systems as Activity Status Monitoring. The devices that hold the sensors may vary though. Devices such as BodyMedia's fit system device and the Mytrak M2 are portable weight loss recreational fitness devices.

The Polar FA20 activity tracker for example can also be used to determine calories burned. There are 2 wrist devices built by Adidas and Nike known as the micoach Zone and the Nike Sportband which also contain accelerometers.

Weight loss may include the use of machines that can simulate altitude change (going up or down a hill) in various mechanical ways (like using a predetermined incline) for determining gradient or slope in equipment like treadmills Treadmill manufacturers can preset inclines on their treadmills and program them to show various inclines based on an inbuilt program or through manual adjustment by the user. There are now various flash thumb drive USB plug-in devices that record training conducted on treadmills and other gym equipment.

8.3 Running Classification

Running has a series of classifications very similar to the Activity Status Monitoring and Weight Loss. The inactive classification is the same as the Inactive Upright classification for both previous classification systems.

The other classifications: Easy, Rolling Hills, Hills, Long Climbs, Hill Efforts, Up Tempo, Anaerobic Threshold, Sprints and Overspeed use altitude change and intensity (speed, power or heart rate) and can use stride rate as another method of determining intensity for classification of activity types.

Altitude Change

All the classifications incorporate the sensors in the same way as mentioned above in Activity Status Monitoring. Devices that contain a barometer or GPS can all determine altitude change like the Suunto and Polar Products as well as Mobimotion. A DEM can be used with any GPS compliant device like a mobile phone and altitude can be determined from GPS as in the Garmin devices.

Intensity

Speed

Devices like the Nike+, Nike Sportband, Adidas micoach Zone and Pacer, Suunto and Polar devices which contain accelerometers are designed to measure running speed. Mobimotion, FRWD and Polar G3 GPS devices and phone applications that utilize internal or external GPS for determining speed like Bones in Motion, AllsportGPS and imap-myrun are also specially designed for running.

Health Applications like Fitbit, Fitlinxx Actiped and Directlife, Bodymedia's Fit system, Mytrak's M2 and Polar's FA20 are not designed for running.

Heart Rate

The basis of Heart Rate sensor technology does not change with use in different sports and is therefore the same as Activity Status Monitoring.

Stride Rate

As above, Stride Rate can also be used as another form of intensity measure utilizing an accelerometer in a speed pod like the Polar RS800 or an accelerometer contained in a phone.

Adidas measure stride rate using a waist mounted Pacer and the wrist version known as the Zone.

The Running classification 'Overspeed' requires altitude change, intensity AND stride rate for classification.

8.4 Field Sports

Field sports have some demand for altitude change (determining the fact that the player is jumping vertically, horizontally or is on the ground.) Very accurate understandings of speed and speed change are also vital to analysis of activity.

Field sports can use exactly the same technology as the running descriptions above with 2 extra possibilities.

Players can wear transmitters that can be triangulated on the side of the playing field by receivers that can be used to calculate speed. Sophisticated video motion capture can be used to do the same thing.

A digital compass may also be employed to measure prescription the user is facing and therefore the user's movement (i.e. backwards, lateral etc).

8.5 Rowing and Kayaking:

Rowing and kayaking once again have no need for a measure of altitude change to ascertain resistance so stroke rate is substituted for measuring altitude change. Inactive, Easy, Slow Full Pressure, Tempo Load, Up Tempo, Anaerobic Threshold, Starts and Moves are all measured in the same way.

Stroke Rate:

Stroke rate is usually measured in rowing based on a magnet being attached to and under the rowers moving seat and a sensor is placed in the boat directly below the seat. A stroke is sensed every $2^{nd}$ time the magnet passes over the sensor. This count is then measured versus one minute which provides the ability to measure strokes per minute. Strokes per minute can be measured more directly at the rigger, by force sensors in the blade of the oar, or by the increase in boat oscillation speed, or be change in force measured by an accelerometer as the rower takes a stroke.

Similar methods can be applied to Swimming as evidenced by the Speedo Strokz Stroke Counter that was available in the late 1990's.

The seat magnet and sensor is commonplace in rowing and there is now new Surge Rate technology incorporating a 3 axis accelerometer to measure the change in force that denotes a kayaker or rower's stroke, thereby allowing stroke rate to be determined when combined with time as in Nielsen Kellerman Rowing and Kayaking devices like the Stroke Coach, Cox Box and Speed Coach.

Stroke Rate can also be mechanically measured in indoor rowing machines such as a Concept 2 rowing ergometer, by measuring a change in power or speed in the fan used for resistance, by a change in prescription of the chain/cable attached to the rowing handle, or by using the magnet and sensor under the rower's seat.

It may also be possible to fix an accelerometer to a kayaker's paddle shaft to measure the oscillation in the blade entering the water on the left and right sides of the boat.

Intensity:

Speed:

Speed can be measured via GPS or an impeller to measure speed through the water. Speed can be measured for an indoor rowing ergometer by the braking pressure for braked devices or by the speed at which the fan spins at.

Impellers are used in Nielsen Kellerman products like the Stroke Coach, Cox Box and Speed Coach for rowing. The Garmin Forerunner series are often used by kayakers which utilize GPS.

Heart Rate:

Heart rate is measured by a receiver of some kind like a Polar or Garmin heart rate monitor. They can also be incorporated into a device measuring all required data like the receiver used in Concept 2 rowing ergometers taking transmitted heart rate data from a chest strap which is then incorporated into the devices measurement. The Garmin Forerunner 305 and 405 both obtain heart rate data which can be used by Kayakers.

8.6 Cycling: (Applies to Triathlon, Mountain Biking, Road, Track and BMX Cycling)

Cycling incorporates slightly different technology to running in that the data must be obtained from a bicycle.

The same basic concept applies as it did for running in that the user must use a combination of altitude change and intensity with an extra classification being cadence.

The following classifications require altitude change and Intensity; Easy, Rolling Hills, Hills, Long Climbs, Hill Efforts, Up Tempo, and Anaerobic Threshold.

The following classifications require altitude change, Intensity and cadence; Flat Big Gear, Big Gear Time Trial, Power, and Sprint.

Altitude Change:

Altitude change can be determined in exactly the same way as in running through a barometer, GPS, DEM or inclinometer. In this case inclination can be used very effectively when mounted on a bicycle which is perfectly level on the flat. Devices like the Sigma BC 2209 MHR and Garmin Edge 705 contain a barometer for altitude measure. The Sigma Rox 8.0 uses an inclinometer as well as a barometer to measure slope or gradient.

There are various cycle ergometers which use various systems to create the equivalent of altitude change. These can be complete bike ergometers or machines that a bike is placed into. The cycle simulator manufacturers can program their devices to increase resistance to simulate gradient or slope through mechanical braking (e.g. Monarch and Cateye CS1000) or electronic braking (e.g. Tracx and Computrainer) and can also use real incline change.

Intensity:

Speed:

Speed for cycling is achieved by attaching a magnet to a spoke on the front or rear wheel of the bike of known circumference and each time the magnet passes a sensor on the forks or rear stay on the bike the distance is added. The distance versus time gives speed. Speed can also be measured through GPS and even converted back through power or calculated from wind speed. Most bike computers use a magnet on the spokes like the Polar CS300. Indirectly it would be possible to calculate speed from knowing the gear the rider is in.

Power:

Power is usually a direct measure in cycling. Power measurement for cycling was pioneered by SRM who use strain gauges attached to the large front sprockets (chainrings) at the bottom bracket attached to the pedal cranks. PowerTap use a system originally used in the Look Max One where the power is measured in the hub of the rear wheel. Ergomo use power measured from the bottom bracket directly.

There have been several indirect measurements of power most notably being the Polar system (e.g. 625X or 725 products) which measures the strain on the chain as the cyclist is riding. Other cycle computers indirectly compute power by measuring a combination of speed, weight and slope or gradient.

An indirect way of assessing power is present in the Shimano Flight Deck and in the Australian Institute of Sport system which measures the gear that the rider is in allowing a calculation of distance per pedal stroke. In each case the gear that the rider is in, is known and the distance for each gear for a pedal turn is fixed.

Heart Rate:

Heart rate measurement is available on many cycle computers (e.g. Polar CS300, Sigma Rox 8.0, SRM).

Cadence or Distance Per Pedal Stroke:

Cadence is a useful extra measure which usually involves a magnet on the pedal arm (crank) passing a sensor on the chain stay of the bike. This can indicate one pedal revolution and when used in conjunction with time creates a pedal cadence measure in revolutions per minute. Distance per pedal stroke is another very useful measure that can be calculated by knowing the gear that the rider is in (e.g. Shimano Flight Deck) or by knowing the distance travelled in a pedal revolution which involves a cadence measure and a distance measure (which is based on the speed measure).

The SRM system incorporates altitude change, speed, power, heart rate and cadence as measures for example.

8.7 Horse Training

Horse training is the relationship in most cases between heart rate and speed or power and terrain is used occasionally.

For Inactive, Walk, Trot, Canter, Gallop, Fast Gallop and Sprint the following combination of Speed or Power and Heart Rate applies:

Speed:

Speed for horse training is measured through GPS devices like GPS-Speed Genie GT31, the GPSsports Spi Pro or FRWD. Theoretically a speed pod may become available for horses. For trotting a magnet can be fixed to a wheel and a sensor can be fitted to the sulky to calculate speed.

Power:

Power could potentially be employed for horses but currently there is no such product.

Intensity:

Heart Rate:

Heart rate has been measured for horses for over 15 years using various Polar Equine Heart Rate monitors like the Polar Equine RS800CX G3 or the CS600X for trotting.

Stride Rate and Length would also make excellent data for classification but are as yet unavailable.

Hill Efforts combines terrain (a change in altitude as discussed previously) and speed, power or heart rate.

8.8 Pedometer Monitoring:

Pedometer monitoring uses a multi axis accelerometer which can be found in smart phones but may also be present in other Pedometer like devices such as the Polar FA20, the Directlife system, Fitbit, Fitlinxx Actiped, Bodymedia's Fit system and Mytrak's M2 device which all track movement.

System Requirements

It will be appreciated that the system of the invention may be implemented on any suitable hardware system, platform or architecture. The hardware system may be provided on-board a device used by the user or on a remote server for example, and preferably comprises at least a processor for running the classification system and in particular the algorithms, at least one memory component for storing at least the algorithms and the threshold criteria, and interface circuitry for communicating with external components that either directly or indirectly provide sensor output data. It will be appreciated that the processor may be any form of programmable hardware device, whether a CPU, Digital Signal Processor, Field-Programmable Gate Array, Microcontroller, Application-Specific Integrated Circuit, or the like.

There are 3 possible configurations for housing the classification system.

The data is processed 'on board' a measurement device (i.e. the classification system is within the measurement/monitoring device), Data is processed via manual (controlled by user) or automatic transfer (upload and download) of data via a communications network (e.g. telecommunications, wifi etc) to a remote server that contains the classification system, or manual or automatic transfer of data to a home computer that either contains the system or that transfers (upload and download) the data to a remote server that contains the system.

The system may house the infrastructure for the Data Acquisition Module, Classification Engine, Compliance Engine, Performance Engine, Training Plan Generator and Alert Generator. This may also allow a person, trainer or coach to input the one or more parameters and/or the one or more associated thresholds that define an activity.

Figure 9:
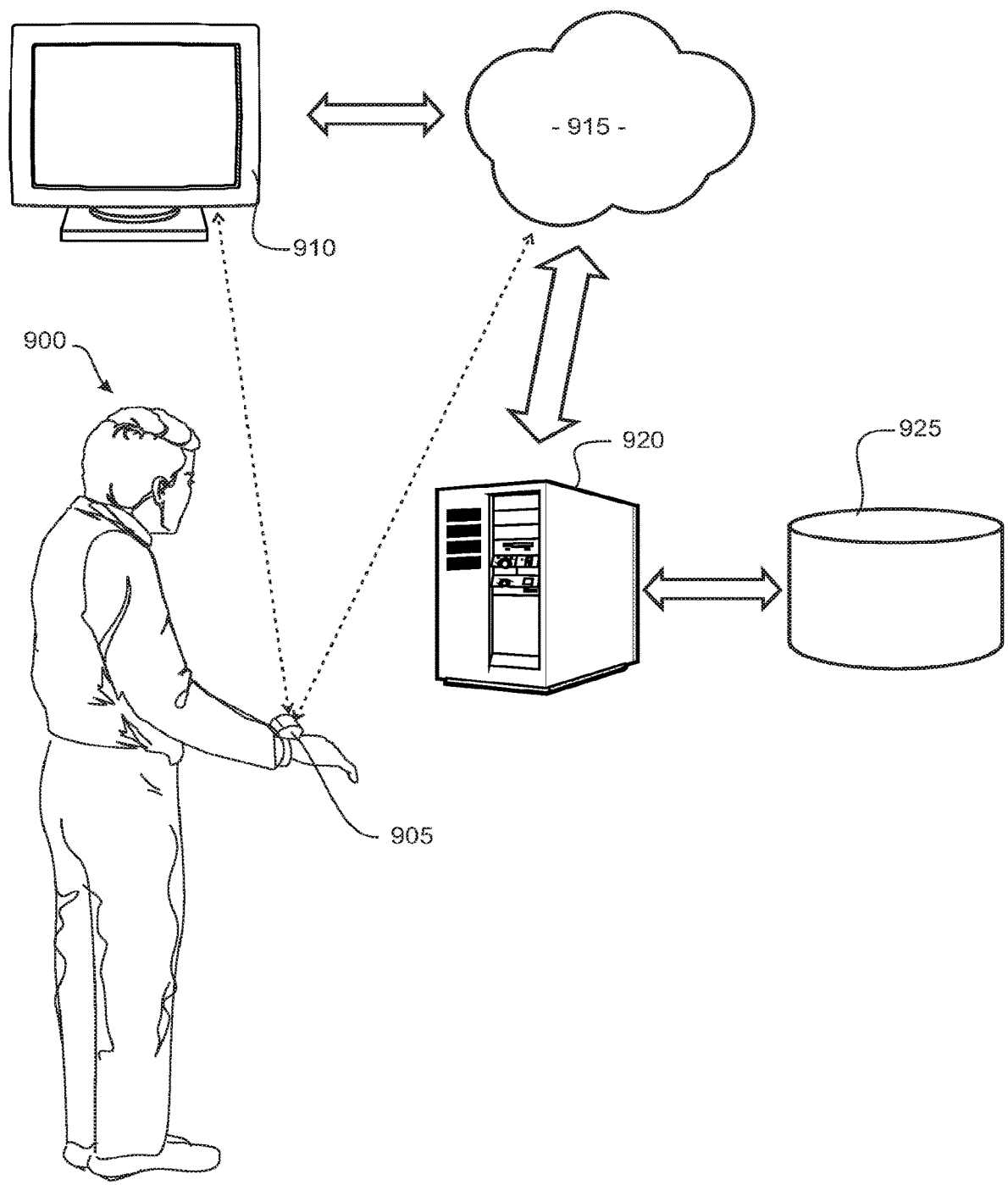
FIG. 9 is a block diagram showing the components associated with the system of the invention.

FIG. 9 shows an exemplary diagram of a user 900 exercising or engaging in one or more activities (i.e. engaging in an activity session) whilst wearing one or more data measurement devices 905 (which can be any combination of devices as explained in the sensor types section above). The data measurement device(s) 905 collect information on the activity session and in particular data streams associated with the parameters required to classify the activities performed during the user's exercise/activity session. The data measurement device(s) 905 may automatically process the data 'on board' (or manually when the user prompts the device to process the data for example) if the Classification Engine is housed within the monitoring device(s). Alternatively or in addition the data may be automatically sent over to an analysis system 920 (which may reside in a remote server or a home computer), either wirelessly or via cables, and if sent to a remote server preferably e.g. via a network. Instead of automatic transmission of the data, the user may upload the data manually to a home computer 910 connected to the analysis system 920 via a network 915 or even directly to a remote server where the analysis system resides. The system (whether in the data measurement device, personal computer or remote server or elsewhere) processes the data by accessing memory 925 (again this may be in the monitoring device, personal computer or remote server and is not necessarily in the same place as the processing circuitry) containing the classification system algorithms and threshold criteria (and preferably user information) to determine the activities conducted and the level of performance as described above. The system 920 may then interpret this data and any other activity data provided by the devices 905 to provide feedback to the user and/or alter a training program stored in memory 925. The analysis system 920 may communicate to the user's computer or devices 905 via any communication means known in the art.

The invention is also intended to cover a method of analysing an exercise session as employed by the system described above.

The foregoing description of the invention includes preferred forms thereof. Modifications may be made thereto without departing from the scope of the invention.

What is claimed is:

1. A method comprising:

receiving, by a processor, activity data of one or more sensors that is indicative of an activity of a user, the activity data comprising a plurality of sensor measurements associated with multiple parameters monitored during an activity session;

retrieving a set of criteria that comprises thresholds to detect an activity type, wherein the set comprises a criterion related to a biomedical parameter and a criterion related to a resistance parameter;

classifying, by the processor based on the set of criteria, the received activity data of the one or more sensors into one or more segments, wherein the one or more segments comprise a first segment comprising a portion of the activity data corresponding to the activity type;

accessing historical data associated with the user, the historical data comprising a second segment of historical data corresponding to the activity type;

comparing the first segment comprising the portion of the received activity data and the second segment comprising historical data; and generating output based on the comparing.

2. The method of claim 1 further comprising determining a performance value for the activity type based on the comparing of the first segment and the second segment.

3. The method of claim 2 wherein the output comprises an alert that is provided to the user during the activity session, wherein the activity session corresponds to a planned workout.

4. The method of claim 3 wherein the alert comprises one or more of a performance measure based on the performance value for the activity type, an instruction to modify the activity of the user during the activity session, or a modification to a training plan for the planned workout.

5. The method of claim 1 wherein the biomedical parameter comprises at least one of electrocardiograph (ECG), blood pressure (BP), body temperature, oxygen saturation, respiration rate, energy expenditure, or oxygen uptake.

6. The method of claim 1 wherein the resistance parameter comprises one of altitude, slope, gradient, stride rate, stroke rate, step rate, cadence, or distance per limb turnover.

7. The method of claim 1 wherein the activity session comprises activities associated with a plurality of different activity types, and further comprising detecting the plurality of activity types of the activity session by comparing the received activity data with a plurality of sets of criteria, wherein each of the plurality of sets corresponds to a multi-parameter zone for an activity type.

8. The method of claim 1 wherein the classifying comprises analyzing one or more measurements associated to the resistance parameter to determine an increase in altitude, a decrease in altitude, or a constant altitude.

9. The method of claim 1 wherein one of the multiple parameters comprises an effort parameter monitored during the activity session, wherein the effort parameter comprises one of a heart rate, a speed, a heart rate variability, a power, an acceleration, and a force.

10. The method of claim 1 wherein one of the multiple parameters comprises a biomechanical parameter, wherein the biomechanical parameter comprises one of vertical oscillation, leg power balance, arm power balance, power through range of motion, foot strike impact, time on ground, and foot strike pattern.

11. The method of claim 1 wherein the resistance parameter is based on a turnover parameter and wherein the turnover parameter comprises one of stride rate, cadence, and stroke rate.

12. The method of claim 1 wherein one of the multiple parameters comprises an environmental parameter, wherein the environmental parameter comprises one of temperature, humidity, and wind speed.

13. The method of claim 1 wherein the classifying further comprises comparing measurements of the received activity data against at least one lower threshold of the set and at least one upper threshold of the set.

14. The method of claim 1 further comprising:

accessing a training plan corresponding to the activity session, wherein the training plan indicates one or more activity types;

comparing at least some of the plurality of measurements of the received activity data to one or more measurements of the training plan; and determining conformity with the training plan based on one or more of duration, distance, intensity, number of distinct activity types, number of instances of an activity type, and rest periods between activity types.

15. The method of claim 1 further comprising determining one or more physiological performance measures for the user based on the comparing, wherein the one or more physiological performance measures comprise one or more of cardiovascular, neurocardio, and muscular performance measures.

16. The method of claim 1 further comprising determining an overall performance measure in view of the comparing of the first segment of the received activity data and the second segment of historical data, wherein the overall performance measure is based on scores assigned to one or more of endurance, strength endurance, and speed.

17. A non-transitory tangible computer readable storage medium having stored thereon computer-executable instructions that, when executed by a processor, cause the processor to:

receive activity data of one or more sensors that is indicative of an activity of a user, the activity data comprising a plurality of sensor measurements associated with multiple parameters monitored during an activity session;

retrieve a set of criteria that comprises thresholds to detect an activity type, wherein the set comprises a criterion related to a biomedical parameter and a criterion related to a resistance parameter;

classify, based on the set of criteria, the received activity data of the one or more sensors into one or more segments, wherein the one or more segments comprise a first segment comprising a portion of the activity data corresponding to the activity type;

access historical data associated with the user, the historical data comprising a second segment of historical data corresponding to the activity type;

compare the first segment comprising the portion of the received activity data and the second segment comprising historical data; and generate output based on the comparing.

18. The non-transitory tangible computer readable storage medium of claim 17 wherein the instructions further cause the processor to determine a performance value for the activity type based on the comparing of the first segment and the second segment.

19. The non-transitory tangible computer readable storage medium of claim 18 wherein the output comprises an alert that is provided to the user during the activity session, wherein the activity session corresponds to a planned workout.

20. The non-transitory tangible computer readable storage medium of claim 19 wherein the alert comprises one or more of a performance measure based on the performance value for the activity type, an instruction to modify the activity of the activity session, or a modification to a training plan for the planned workout.

21. The non-transitory tangible computer readable storage medium of claim 18 wherein the biomedical parameter comprises at least one of electrocardiograph (ECG), blood pressure (BP), body temperature, oxygen saturation, respiration rate, energy expenditure, or oxygen uptake.

22. The non-transitory tangible computer readable storage medium of claim 18 wherein the resistance parameter comprises one of altitude, slope, gradient, stride rate, stroke rate, cadence, or distance per limb turnover.

23. The non-transitory tangible computer readable storage medium of claim 18 wherein the activity session comprises activities associated with a plurality of different activity types, and wherein the instructions further cause the processor to detect the plurality of activity types of the activity session by comparing the received activity data with a plurality of sets of criteria, wherein each of the plurality of sets corresponds to a multi-parameter zone for an activity type.

24. A system comprising:
a memory; and
a processor operatively coupled to the memory, the processor to execute instructions to:
receive activity data of one or more sensors that is indicative of an activity of a user, the activity data comprising a plurality of sensor measurements associated with multiple parameters monitored during an activity session;
retrieve a set of criteria that comprise thresholds to detect an activity type, wherein the set comprises a criterion related to a biomedical parameter and a criterion related to a resistance parameter;
classify, based on the set of criteria, the received activity data of the one or more sensors into one or more segments, wherein the one or more segments comprise a first segment comprising a portion of the activity data corresponding to the activity type;
access historical data associated with the user, the historical data comprising a second segment of historical data corresponding to the activity type;
compare the first segment comprising the portion of the received activity data and the second segment comprising historical data; and
generate output based on the comparing.

25. The system of claim 24 wherein the processor is further to determine a performance value for the activity type based on the comparing of the first segment and the second segment.

26. The system of claim 25 wherein the output comprises an alert that is provided to the user during the activity session, wherein the activity session corresponds to a planned workout.

27. The system of claim 26 wherein the alert comprises one or more of a performance measure based on the performance value for the activity type, an instruction to modify the activity of the user during the activity session, or a modification to a training plan for the planned workout.

28. The system of claim 24 wherein the biomedical parameter comprises at least one of electrocardiograph (ECG), blood pressure (BP), body temperature, oxygen saturation, respiration rate, energy expenditure, or oxygen uptake.

29. The system of claim 24 wherein the resistance parameter comprises one of altitude, slope, gradient, stride rate, stroke rate, cadence, or distance per limb turnover.

30. The system of claim 24 wherein the activity session comprises activities associated with a plurality of different activity types, and wherein the processor is further to detect the plurality of activity types of the activity session by comparing the received activity data with a plurality of sets of criteria, wherein each of the plurality of sets corresponds to a multi-parameter zone for an activity type.

* * * * *